United States Patent
Repasi et al.

(10) Patent No.: US 11,891,455 B2
(45) Date of Patent: Feb. 6, 2024

(54) POLYMORPH FORM OF (R)-2-[2-AMINO-3-(INDOL-3-YL)PROPIONYLAMINO]-2-METHYLPROPIONIC ACID AND USES THEREOF

(71) Applicant: Galimedix Therapeutics Inc., Kensington, MD (US)

(72) Inventors: Jozsef Repasi, Erd (HU); Andras Szabo, Budapest (HU); Markus Henrich, Münzenberg (DE)

(73) Assignee: Galimedix Therapeutics Inc

( * ) Notice: Subject to any disclaimer, the term of this patent is extended or adjusted under 35 U.S.C. 154(b) by 0 days.

(21) Appl. No.: 17/762,873

(22) PCT Filed: Sep. 23, 2020

(86) PCT No.: PCT/IB2020/058861
§ 371 (c)(1),
(2) Date: Mar. 23, 2022

(87) PCT Pub. No.: WO2021/059142
PCT Pub. Date: Apr. 1, 2021

(65) Prior Publication Data
US 2022/0389056 A1  Dec. 8, 2022

Related U.S. Application Data

(60) Provisional application No. 62/904,339, filed on Sep. 23, 2019.

(51) Int. Cl.
*C07K 5/078* (2006.01)
*A61P 27/06* (2006.01)

(52) U.S. Cl.
CPC .......... *C07K 5/06156* (2013.01); *A61P 27/06* (2018.01); *C07B 2200/13* (2013.01)

(58) Field of Classification Search
None
See application file for complete search history.

(56) References Cited

U.S. PATENT DOCUMENTS

2006/0234947 A1  10/2006  Gazit
2014/0199738 A1  7/2014  Woo et al.

FOREIGN PATENT DOCUMENTS

EP        2595625 B1    4/2016
WO    WO 2012/010415    1/2012

OTHER PUBLICATIONS

Abramov et al. "Amyloid-β as a positive endogenous regulator of release probability at hippocampal synapses" Nature neuroscience. Dec. 2009;12(12):1567-76.
Alzheimer A. "Ueber eine einartige Erkrankung der Himrinde" Zblatt fur ges Neurologie u Psychiatrie. 1907;18:177-9.
Bao et al. "Different β-amyloid oligomer assemblies in Alzheimer brains correlate with age of disease onset and impaired cholinergic activity" Neurobiology of aging. Apr. 1, 2012;33(4):825-e1.
Barghorn et al. "Globular amyloid β-peptide1—42 oligomer—a homogenous and stable neuropathological protein in Alzheimer's disease" Journal of neurochemistry. Nov. 2005;95(3):834-47.
Blanks et al. "Retinal pathology in Alzheimer's disease. II. Regional neuron loss and glial changes in GCL" Neurobiology of aging. May 1, 1996;17(3):385-95.
Charoenkwan et al. "SCMCRYS: predicting protein crystallization using an ensemble scoring card method with estimating propensity scores of P-collocated amino acid pairs" PloS one. Sep. 3, 2013;8(9):e72368.
Citron M. "Alzheimer's disease: strategies for disease modification" Nature reviews Drug discovery. May 2010;9(5):387-98.
Demuro et al. Calcium signaling and amyloid toxicity in Alzheimer disease Journal of Biological Chemistry. Apr. 23, 2010;285(17):12463-8.
Dentchev et al. "Amyloid-β is found in drusen from some age-related macular degeneration retinas, but not in drusen from normal retinas" American journal of ophthalmology. May 14, 2003;136(4):787 -.
Ferreira et al. "Aβ toxicity in primary cultured neurons" In Alzheimer's Disease and Frontotemporal Dementia 2010 (pp. 141-153). Humana Press, Totowa, NJ.
Ferreira et al. "The Aβ oligomer hypothesis for synapse failure and memory loss in Alzheimer's disease" Neurobiology of learning and memory. Nov. 1, 2011;96(4):529-43.
Ferreira et al. "Soluble protein oligomers as emerging toxins in Alzheimer's and other amyloid diseases" IUBMB life. 2007;59(4-5):332-45.
Friedman et al. "Prevalence of Open-Angle Glaucoma among Adults in the United States" Arch Ophthalmol. Apr. 2004;122(4):532-8.
Giuffrida et al. "β-amyloid monomers are neuroprotective" Journal of Neuroscience. Aug. 26, 2009;29(34):10582-7.
Givand et al. "Effect of relative solubility on amino acid crystal purity" AIChE journal. Dec. 2001:47(12):2705-12.
Goldblum et al. "Distribution of amyloid precursor protein and amyloid-β immunoreactivity in DBA/2J glaucomatous mouse retinas" Investigative ophthalmology & visual science. Nov. 1, 2007;48(11):5085-90.
Gramlic et al. (2012). "Proteochemical and immunohistochemical analysis reveals ß- Amyloid deposition in human glaucomatous retinae" ARVO poster, IOVS.
Guo et al. "Targeting amyloid-β in glaucoma treatment" Proceedings of the National Academy of Sciences. Aug. 14, 2007;104(33):13444-9.
Hageman et al. "Age-related macular degeneration (AMD)" Webvision: The Organization of the Retina and Visual System [Internet]. Jan. 1, 2008.

(Continued)

*Primary Examiner* — Christina Bradley
(74) *Attorney, Agent, or Firm* — Mark S. Cohen; PEARL COHEN ZEDEK LATZER BARATZ LLP

(57) ABSTRACT

This intention relates to a novel polymorph form of compound (R)-2-[2-amino-3-(indol-3-yl)propionylamino]-2-methylpropionic acid, a process for making the novel polymorph form of the compound, and uses thereof for making other polymorph forms of the compound. The invention further relates to composition comprising novel polymorph form of the compound and a pharmaceutically acceptable carrier or excipient.

14 Claims, 11 Drawing Sheets

(56) References Cited

OTHER PUBLICATIONS

Hardy et al. "Alzheimer's disease: the amyloid cascade hypothesis" Science. Apr. 10, 1992;256(5054):184-5.
Hoh Kam et al. "Viewing ageing eyes: diverse sites of amyloid Beta accumulation in the ageing mouse retina and the up-regulation of macrophages" PloS one. Oct. 1, 2010:5(10):e13127.
International Search Report for PCT Application No. PCT/IB2020/058861 dated Dec. 15, 2000.
Iseri et al. "Relationship between cognitive impairment and retinal morphological and visual functional abnormalities in Alzheimer disease" Journal of neuro-ophthalmology. Mar. 1, 2006;26(1):18-24.
Jia et al. "Effect of general anesthetics on IOP in rats with experimental aqueous outflow obstruction" Investigative ophthalmology & visual science. Oct. 1, 2000:41(11):3415-9.
Johnson et al. "The Alzheimer's Aβ-peptide is deposited at sites of complement activation in pathologic deposits associated with aging and age-related macular degeneration" Proceedings of the National Academy of Sciences. Sep. 3, 2002;99(18):11830-5.
Kipfer-Kauer et al. "Distribution of amyloid precursor protein and amyloid-β in ocular hypertensive C57BL/6 mouse eyes" Current eye research. Sep. 1, 2010;35(9):828-34.
Klein et al. "Ten-year incidence and progression of age-related maculopathy: The Beaver Dam eye study" Ophthalmology. Oct. 1, 2002;109(10):1767-79.
Lacor et al. "Aβ oligomer-induced aberrations in synapse composition, shape, and density provide a molecular basis for loss of connectivity in Alzheimer's disease" Journal of Neuroscience. Jan. 24, 2007;27(4):796-807.
Lesné et al. "A specific amyloid-β protein assembly in the brain impairs memory" Nature. Mar. 2006;440(7082):352-7.
McKinnon SJ. "Glaucoma: ocular Alzheimer's disease?" Frontiers in Bioscience-Landmark. Sep. 1, 2003;8(6):1140-56.
McKinnon et al. "Caspase activation and amyloid precursor protein cleavage in rat ocular hypertension" Investigative ophthalmology & visual science. Apr. 1, 2002;43(4):1077-87.
Ning et al. "Amyloid-β deposits lead to retinal degeneration in a mouse model of Alzheimer disease" Investigative ophthalmology & visual science. Nov. 1, 2008;49(11):5136-43.
Ohno-Matsui K. "Parallel findings in age-related macular degeneration and Alzheimer's disease" Progress in retinal and eye research. Jul. 1, 2011;30(4):217-38.
Palomo JM. "Solid-phase peptide synthesis: an overview focused on the preparation of biologically relevant peptides" Rsc Advances. 2014;4(62):32658-72.
Parisi et al. "Morphological and functional retinal impairment in Alzheimer's disease patients" Clinical neurophysiology. Oct. 1, 2001:112(10):1860-7.
Parsons et al. "MRZ-99030—A novel modulator of Aβ aggregation: I-mechanism of action (MoA) underlying the potential neuroprotective treatment of Alzheimer's disease, glaucoma and age-related macular degeneration (AMD)" Neuropharmacology. May 1, 2015;92:158-69.
Puzzo D, Privitera L, Leznik E, Fa M, Staniszewski A, Palmeri A, Arancio O. Picomolar amyloid-β positively modulates synaptic plasticity and memory in hippocampus. Journal of Neuroscience. Dec. 31, 2008;28(53):14537-45.
Rogers et al. "Complement activation by beta-amyloid in Alzheimer disease" Proceedings of the National Academy of Sciences. Nov. 1, 1992;89(21):10016-20.
Schlenzig et al. "Pyroglutamate formation influences solubility and amyloidogenicity of amyloid peptides" Biochemistry. Jul. 28, 2009;48(29):7072-8.
Selkoe DJ. "Soluble oligomers of the amyloid β-protein: Impair synaptic plasticity and behavior" Synaptic Plasticity and the Mechanism of Alzheimer's Disease. 2008:89-102.
Sivak JM. "The aging eye: common degenerative mechanisms between the Alzheimer's brain and retinal disease" Investigative ophthalmology & visual science. Jan. 1, 2013;54(1):871-80.
Spencer et al. "A newcomer' s guide to peptide crystallography" Israel journal of chemistry. Jun. 2015;55(6-7):698-710.
Tsuruma et al. "Induction of amyloid precursor protein by the neurotoxic peptide, amyloid-beta 25-35, causes retinal ganglion cell death" Journal of neurochemistry. Jun. 2010;113(6):1545-54.
Walsh et al. "Amyloid beta peptide causes chronic glial cell activation and neuro-degeneration after intravitreal injection" Neuropathology and applied neurobiology. Oct. 2005;31(5):491-502.
Wang et al. "Amyloid-β up-regulates complement factor B in retinal pigment epithelial cells through cytokines released from recruited macrophages/microglia: Another mechanism of complement activation in age-related macular degeneration" Journal of cellular physiology. Jul. 2009;220(1):119-28.
Wilcox et al. "Aβ oligomer-induced synapse degeneration in Alzheimer's disease" Cellular and molecular neurobiology. Aug. 2011;31(6):939-48.
Xia W. "Brain amyloid β protein and memory disruption in Alzheimer's disease" Neuropsychiatric disease and treatment. 2010;6:605.
Yoneda et al. "Vitreous fluid levels of β-amyloid (1-42) and tau in patients with retinal diseases" Japanese journal of ophthalmology. Mar. 2005;49(2):106-8.
Yoshida et al. "The potential role of amyloid β in the pathogenesis of age-related macular degeneration" The Journal of clinical investigation. Oct. 3, 2005;115(10):2793-800.
Zhu et al. "Muscarinic activation attenuates abnormal processing of β-amyloid precursor protein induced by cobalt chloride-mimetic hypoxia in retinal ganglion cells" Biochemical and biophysical research communications. Jun. 19, 2009;384(1):110-3.

POLYMORPH FORM OF (R)-2-[2-AMINO-3-(INDOL-3-YL)PROPIONYLAMINO]-2-METHYLPROPIONIC ACID AND USES THEREOF

FIELD OF THE INVENTION

This invention relates to a novel polymorph form of compound (R)-2-[2-amino-3-(indol-3-yl)propionylamino]-2-methylpropionic acid, a process for making the novel polymorph form of the compound, and uses thereof for making other polymorph forms of the compound.

BACKGROUND OF THE INVENTION

Glaucoma and age-related macular degeneration (AMD) are leading causes of progressive vision loss and blindness worldwide with the incidence and prevalence of each disease increasing substantially with age. As with Alzheimer's disease (AD), both conditions have a strong age-related incidence and chronic neurodegenerative changes seen in the eyes of glaucoma and AMD patients are similar to changes characteristic of the brains of the AD patient. AMD and glaucoma have a common link in that the presence of toxic amyloid beta (Aβ) oligomers is associated with disease progression.

(R)-2-[2-Amino-3-(indol-3-yl)propionylamino]-2-methylpropionic acid is a dipeptide containing D-tryptophan and 2-amino-2-methylpropionic acid, which acts as a modulator of Aβ aggregation, preventing the formation of toxic oligomeric and fibrillar species, while promoting aggregation into nontoxic off pathway. Currently, (R)-2-[2-Amino-3-(indol-3-yl)propionylamino]-2-methylpropionic acid is in clinical development for the topical treatment of glaucoma and dry age-related macular degeneration (AMD).

Amyloid-beta (Aβ)-associated diseases and conditions include diseases and conditions wherein neuronal and non-neuronal cell function is affected by the presence of toxic Aβ oligomers, which are formed from misfolded Aβ monomers by aggregation. Aβ-associated diseases and conditions include ophthalmic and neurological diseases and conditions for example but not limited to Alzheimer's disease (AD), glaucoma, and age-related macular degeneration of the retina.

AD is the most common form of dementia and its incidence is increasing at an alarming rate all over the world. The pathophysiology of AD is characterized by chronic, progressive neurodegeneration which involves early synaptotoxicity. One of the most obvious pathological features of AD is the accumulation of deposited Aβ in the brain. While normal Aβ is vital to proper neural function, misfolded versions of Aβ often associate with overproduction of Aβ, and are thought to underlie early synaptic pathology. Thus, reduction of toxic Aβ oligomers in the brain while not harming normal Aβ function, may be a promising therapeutic strategy in improving or reversing AD-related dysfunction and neurodegeneration.

Studies have shown that glaucoma is the second leading cause of blindness in the United States and is a neurodegenerative disease, with increasing evidence that Aβ toxicity plays an important role in its pathogenesis. The pathologic correlate of glaucoma is the progressive degeneration of retinal ganglion cells (RGC) and their axons which form the optic nerve. The classification of glaucoma includes the following different types: primary angle-closure glaucoma, secondary open-angle glaucoma, steroid-induced glaucoma, traumatic glaucoma, pigmentary dispersion syndrome, pseudoexfoliation syndrome, secondary angle-closure glaucoma, neovascular glaucoma, uveitis and glaucoma and other non-further specified eye pathologies. Recently, Aβ has been found to co-localize with dying retinal ganglion cells. Animal studies also demonstrate that the soluble $Aβ_{1-42}$ oligomers, in particular, are very potent toxins for retinal ganglion cells. Thus, as with AD, Aβ toxicity is thought to play a pivotal role in glaucoma and its associated conditions.

Similarly, dry age-related macular degeneration of the retina (dry AMD) is a condition involving a pathology of the retina which has also been closely associated with the occurrence of Aβ toxicity in retinal pigment epithelium and photoreceptors, and which leads to a progressive loss of vision, leading finally to blindness.

Treatment of Aβ toxicity-related diseases, may in many instances requires life-long treatment. Therefore, purity of compounds used in any treatment is a critical concern, since dosing with compounds containing not well-characterized impurities leads to cumulative doses over decades, associated with unknown risks. This is especially true for oral dosing which, due to the higher doses, would lead to a much higher absolute impurity exposure.

There exists a significant unmet medical need for methods using ultrapure compounds to treat diseases related to Aβ toxicity including Aβ-associated neurodegenerative diseases, for example but not limited to dry AMD, glaucoma, and AD, since dosing with ultrapure compounds may reduce cumulative expose of a subject to toxic impurities present within cumulative doses administered over decades. This is especially true for oral dosing, which, due to higher doses, would lead to a much higher absolute impurity exposure.

SUMMARY OF THE INVENTION

The present invention provides a novel polymorph form of compound (R)-2-[2-amino-3-(indol-3-yl)propionylamino]-2-methylpropionic acid, characterized by an X-ray powder diffraction pattern displaying peaks at ° 2θ (d value Å) angles of 5.87 (15.067), 11.91(7.432), 17.99 (4.931), 30.35 (2.945).

In another aspect, the present invention provides Form II of compound (R)-2-[2-amino-3-(indol-3-yl)propionylamino]-2-methylpropionic acid, characterized by a single crystal X-ray diffraction pattern having an orthorhombic crystal system and a space group of P $2_12_12_1$. In some embodiments, the orthorhombic crystal system has a dimension of a=6.1316(2)Å; b=9.1342(2)Å; and c=25.9213(7)Å.

In another aspect, the present invention provides a process for preparing FormII of compound (R)-2-[2-amino-3-(indol-3-yl)propionylamino]-2-methylpropionic acid of the invention, comprising (a) mixing compound (R)-2-[2-amino-3-(indol-3-yl)propionylamino]-2-methylpropionic acid with an aqueous HCl to provide a solution of the compound; (b) cooling the solution to about 0-5° C., followed by adjusting the pH of the solution to about 5.6 with a base; (c) stirring the solution at about 0-5° C. until precipitation is complete; and (d) isolating the resulting precipitate to give the Form II of compound (R)-2-[2-amino-3-(indol-3-yl)propionylamino]-2-methylpropionic acid.

In another aspect, the present invention provides Form II of compound (R)-2-[2-amino-3-(indol-3-yl)propionylamino]-2-methylpropionic acid as prepared by the processes as described herein.

The present invention provides a method of preparing ultrapure Form I of compound (R)-2-[2-amino-3-(indol-3-yl)propionylamino]-2-methylpropionic acid, characterized by an X-ray powder diffraction pattern displaying peaks at °2θ (d value Å) angles 6.75 (13.095), 10.19 (8.678), 11.76 (7.524), 13.56 (6.531), 17.68 (5.017), 18.63 (4.764), 20.15 (4.407), 22.08 (4.026), wherein the purity of the ultrapure Form I of the compound is from about 99.70 area % to about 99.999 area % by IPC-HPLC, the method comprising (a) mixing Form II of the compound with water to prepare a solution of Form II of the compound;

(b) heating the solution of Form II to about 30-35° C. and cooling to room temperature to produce a precipitate; and (c) isolating and washing the precipitate to give ultrapure Form I of compound (R)-2-[2-amino-3-(indol-3-yl) propionylamino]-2-methylpropionic acid.

The present invention further provides a method for preparing ultrapure Form I, characterized by an X-ray powder diffraction pattern displaying peaks at ° 2θ (d value Å) angles 6.75 (13.095), 10.19 (8.678), 11.76 (7.524), 13.56 (6.531), 17.68 (5.017), 18.63 (4.764), 20.15 (4.407), 22.08 (4.026), wherein said ultrapure Form I has a purity of from about 99.70 area % to about 99.999 area % by IPC-HPLC, the method comprising (a) mixing compound (R)-2-[2-amino-3-(indol-3-yl)propionylamino]-2-methylpropionic acid with an aqueous HCl to provide a solution of the compound;

(b) cooling the solution to about 5-10° C., followed by adjusting the pH of the solution to about 5.6 with a base;

(c) stirring the solution at about 0-5° C. until precipitation is complete;

(d) isolating the resulting precipitate to obtain Form II of the compound;

(e) mixing the Form II of step (d) with water to prepare a solution of the Form II;

(f) heating the solution of the Form II of step (e) to about 30-35° C. and cooling to room temperature to produce a precipitate; and (g) isolating and washing the precipitate to give an ultrapure Form I; wherein the washing step is optionally repeated for two or three times; and (h) optionally repeating steps (a) to (g).

In some embodiments, the compound (R)-2-[2-amino-3-(indol-3-yl)propionylamino]-2-methylpropionic acid of step (a) is prepared by the steps comprising (a) reacting compound (2)

(d)

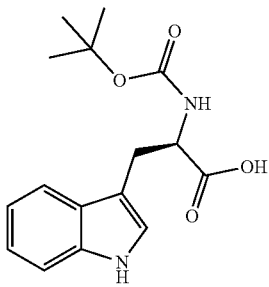

2 with tert-butyl2-aminoisobutyrate (3) in the presence of 4-(4,6-dimethoxy-1,3,5-triazin-2-yl)-4-methylmorpholine chloride (DMTMM) to give compound (4)

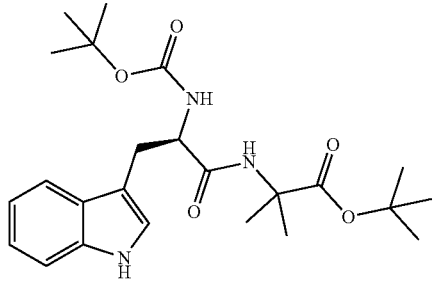

4

(b) removing the Boc groups from compound (4) with hydrogen chloride gas to give compound (5); and

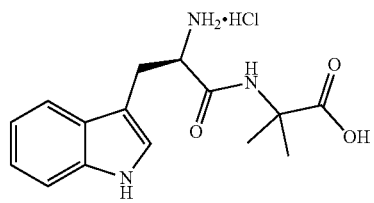

5

(c) providing a solution of compound 5 in water and adjusting the pH of the solution to about 5.5-5.7 to give compound (R)-2-[2-amino-3-(indol-3-yl)propionylamino]-2-methylpropionic acid.

The present invention further provides Form I of (R)-2-[2-amino-3-(indol-3-yl)propionylamino]-2-methylpropionic acid prepared by the method as described herein.

The present invention also provides Form I of (R)-2-[2-amino-3-(indol-3-yl)propionylamino]-2-methylpropionic acid having a purity of from about 99.70 area % to about 99.999 area % by IPC-HPLC.

The present invention further provides a composition comprising ultrapure Form I as prepared by the method described herein and a pharmaceutically acceptable carrier or excipient.

The present invention further provides a formulation comprising ultrapure Form I, hydroxypropylbetadex, citric acid, monohydrate, sodium citrate dihydrate, glycerol, and hypromellose.

The present invention further provides a composition comprising Form II as prepared by the method of the invention as described herein and a pharmaceutically acceptable carrier or excipient.

The present invention further provides a formulation comprising Form II as prepared by the method of the invention as described herein, hydroxypropylbetadex, citric acid, monohydrate, sodium citrate dihydrate, glycerol, and hypromellose.

In a further aspect, the present invention provides a process for preparing Form II of (R)-2-[2-amino-3-(indol-3-yl)propionylamino]-2-methylpropionic acid of claim 1, comprising (a) reacting compound (2)

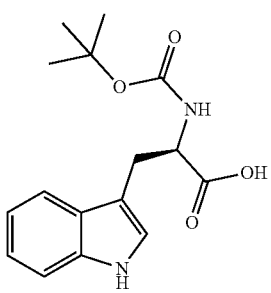

with tert-butyl-2-aminoisobutyrate (3) in the presence of 4-(4,6-dimethoxy-1,3,5-triazin-2-yl)-4-methylmorpholine chloride (DMTMM) to give compound (4)

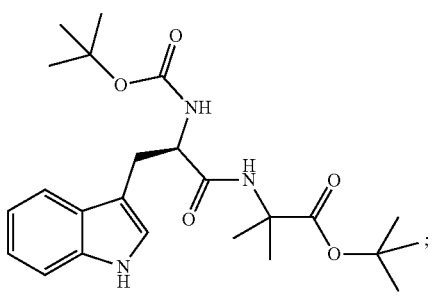

(b) removing the Boc group from compound (4) with hydrogen chloride gas to give compound (5);

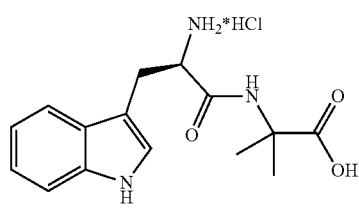

(c) providing a solution of compound (5) in water and adjusting the pH of the solution to about 5.5-5.7 to give a precipitate;
(d) mixing the precipitate from step (c) with an aqueous HCl to provide a solution;
(e) cooling the solution of step (d) to about 0-5° C., followed by adjusting the pH of the solution to about 5.6 with a 20% NaOH aqueous solution
(f) stirring the solution at about 0-5° C. until precipitation is complete; and
(g) isolating the resulting precipitate to give Form II of compound (R)-2-[2-amino-3-(indol-3-yl)propionylamino]-2-methylpropionic acid.

In a further aspect, the present invention provides a method of purifying a crude Form I (stable form) of compound (R)-2-[2-amino-3-(indol-3-yl)propionylamino]-2-methylpropionic acid, comprising (a) mixing said crude Form I of the compound with an aqueous HCl to provide a solution of the crude Form I of the compound; (b) cooling the solution to about 5-10° C., followed by adjusting the pH of the solution to about 5.6 with a base; (c) stirring the solution at about 0-5° C. until precipitation is complete; (d) isolating the resulting precipitate to obtain Form II of compound (R)-2-[2-amino-3-(indol-3-yl)propionylamino]-2-methylpropionic acid; (e) mixing the Form II of the compound of step (d) with water to prepare a solution of Form II of the compound; (f) heating the solution of Form II of step (e) to about 30-35° C. and cooling to room temperature to produce a precipitate; and (g) isolating and washing the precipitate to give a pure Form I of compound (R)-2-[2-amino-3-(indol-3-yl)propionylamino]-2-methylpropionic acid, wherein the washing step is optionally repeated for two or three times; and (h) optionally repeating steps (a) to (g); wherein the purity of the pure Form I of the compound of step (g) is from about 99.0 area % to about 99.9 area % by IPC-HPLC. In a related aspect, the pure Form I compound purified comprises an ultrapure Form I.

In yet another aspect, the present invention provides Form I of (R)-2-[2-amino-3-(indol-3-yl)propionylamino]-2-methylpropionic acid as prepared by the method of invention as disclosed herein.

The present invention further provides Form I of (R)-2-[2-amino-3-(indol-3-yl)propionylamino]-2-methylpropionic acid having a purity of from about 99.0 area % to about 99.9 area % by IPC-HPLC. In a related aspect, the Form I provided comprises an ultrapure Form I.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The present invention relates to a novel polymorph form of compound (R)-2-[2-amino-3-(indol-3-yl)propionylamino]-2-methylpropionic acid.

Compound (R)-2-[2-amino-3-(indol-3-yl)propionylamino]-2-methylpropionic acid is represented by the structure of Formula I

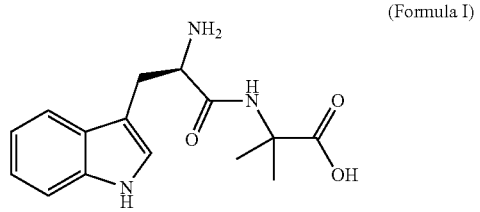 [SMILES: CC(C)(NC(=O)[C@H](N)Cc1c[nH]c2ccccc12)C(=O)O]

(Formula I)

Figure 1:
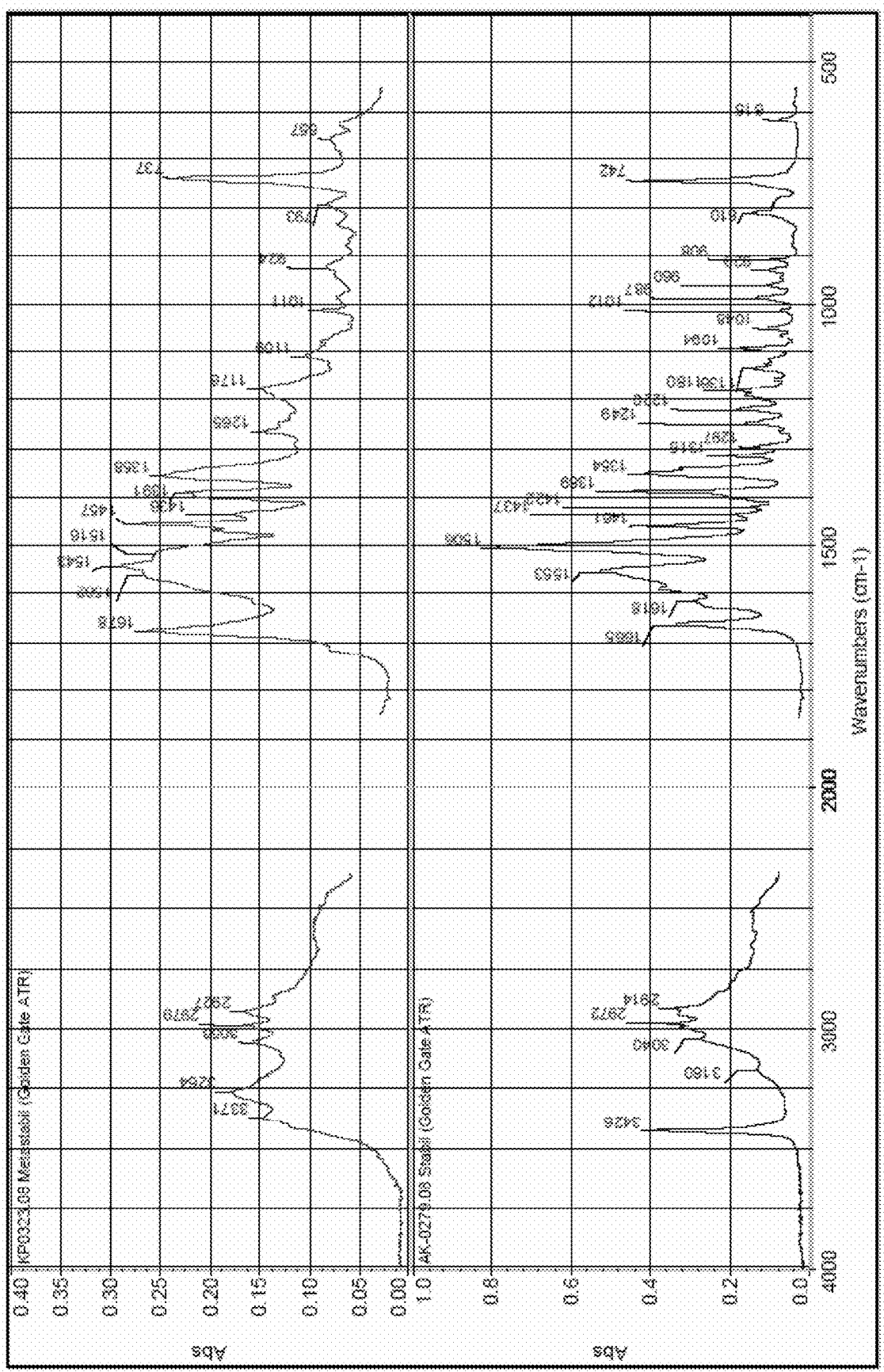
FIG. 1 shows FT-IR spectra for GAL-101 Form I (lower trace) and GAL-101 Form II (upper trace).
Figure 2:
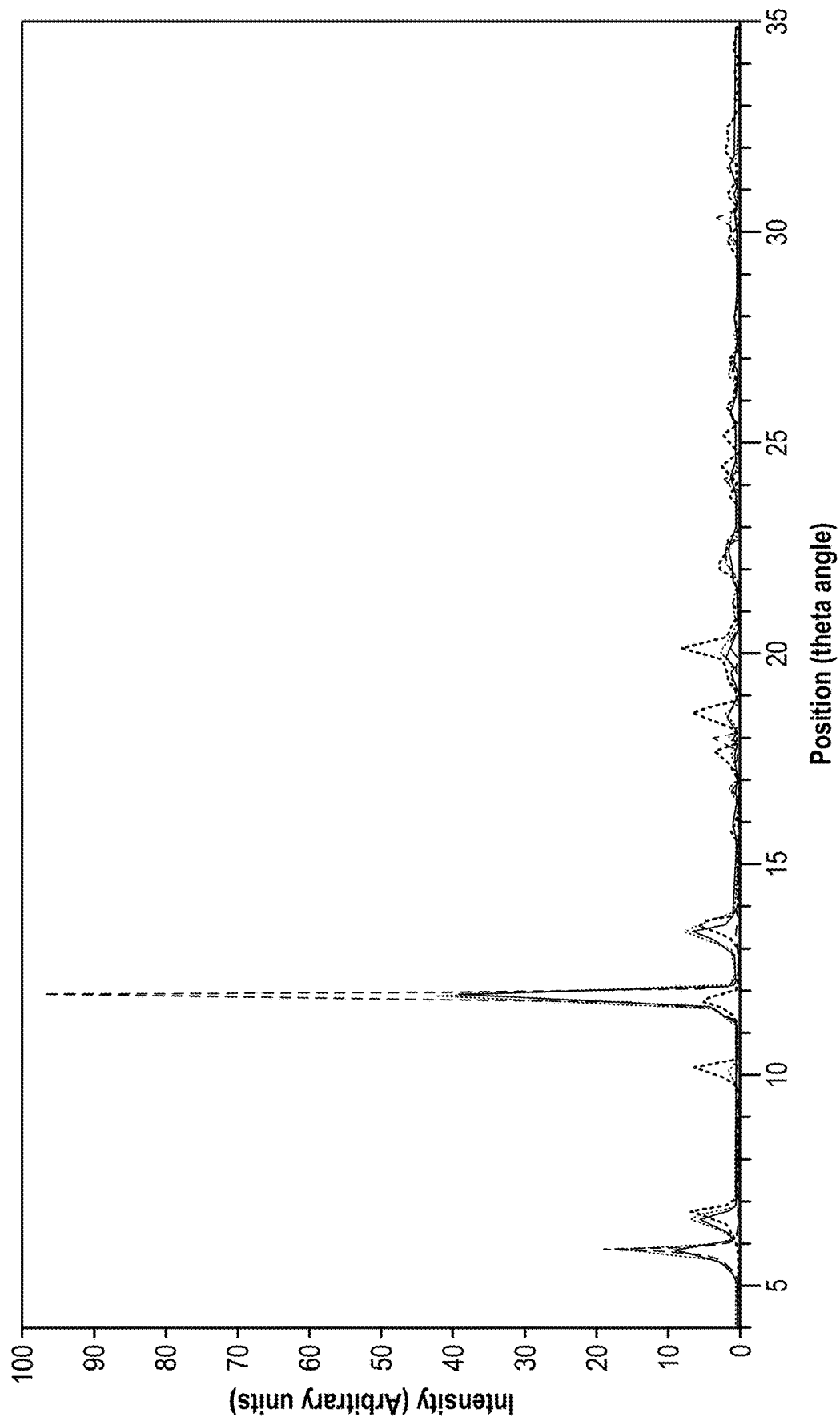
FIG. 2 shows an X-ray powder diffraction diagram (XPRD) for GAL-101 Form I (short dashed line) and GAL-101 Form II (long dashed line), measured at 20-25° C., after heating at 30-35° C. for 15 minutes (solid line) and after heating at 30-35° C. for an additional 60 minutes (dotted line).

In some embodiments, the invention provides Form II of compound (R)-2-[2-amino-3-(indol-3-yl)propionylamino]-2-methylpropionic acid (GAL-101 Form II), characterized by an X-ray powder diffraction pattern displaying peaks at ° 2θ (d value Å) angles of 5.87 (15.067), 11.91(7.432), 17.99 (4.931), 30.35 (2.945). In some embodiments, GAL-101 Form II of the invention exhibits the FT-IR spectrum as shown in FIG. 1. In some embodiments, GAL-101 Form II of the invention exhibits an X-ray powder diffraction pattern as shown in FIG. 2.

In one embodiment, GAL-101 Form II of the invention exhibits essentially the X-ray powder diffraction pattern as shown in Table 1:

TABLE 1

| Peak No. | 2*theta [deg] | D (hkl) [Å] | I(abs) [cts] | I(rel) [%] |
|---|---|---|---|---|
| 1 | 5.87 | 15.067 | 5787 | 18 |
| 2 | 11.91 | 7.432 | 31402 | 100 |
| 3 | 17.99 | 4.931 | 1308 | 4 |
| 4 | 30.35 | 2.945 | 1216 | 4 |

In another aspect, the present invention provides Form II of compound (R)-2-[2-amino-3-(indol-3-yl)propionylamino]-2-methylpropionic acid (GAL-101 Form II), characterized by a single crystal X-ray diffraction pattern having an orthorhombic crystal system and a space group of P $2_12_12_1$. In some embodiments, the orthorhombic crystal system has a dimension of a=6.1316(2)Å; b=9.1342(2)Å; and c=25.9213(7)Å.

In some embodiments, GAL-101 Form II exhibits essentially the single crystal X-ray diffraction pattern as shown in Table 2:

TABLE 2

| Crystal Data | |
|---|---|
| Formula | $C_{15}H_{19}N_3O_3$ |
| Crystal System | Orthorhombic |
| Space group | $P2_12_12_1$ (No. 19) |
| a, b, c [Angstrom] | 6.1316(2), 9.1342(2), 25.9213(7) |
| V [Ang$^3$] | 1451.78(7) |
| Z | 4 |
| D(calc) [g/cm$^3$] | 1.324 |
| Mu(CuKa) [/mm ] | 0.769 |
| Crystal Size [mm] | 0.03 × 0.08 × 0.20 |

In some embodiments, the invention provides Form I (stable form) of compound (R)-2-[2-Amino-3-(indol-3-yl) propionylamino]-2-methylpropionic acid (GAL-101 Form I), exhibiting essentially the X-ray powder diffraction pattern as shown in Table 3:

TABLE 3

| Peak No. | 2*theta [deg] | D (hkl) [Å] | I(abs) [cts] | I(rel) [%] |
|---|---|---|---|---|
| 1 | 6.75 | 13.095 | 2384 | 83 |
| 2 | 10.19 | 8.678 | 2167 | 76 |
| 3 | 11.76 | 7.524 | 1796 | 63 |
| 4 | 13.56 | 6.531 | 1980 | 69 |
| 5 | 17.68 | 5.017 | 1107 | 39 |
| 6 | 18.63 | 4.764 | 2328 | 81 |
| 7 | 20.15 | 4.407 | 2861 | 100 |
| 8 | 22.08 | 4.026 | 929 | 32 |

As used herein, "GAL-101" refers to compound (R)-2-[2-amino-3-(indol-3-yl)propionylamino]-2-methylpropionic acid and includes any polymorph forms thereof.

As used herein, "GAL-101 Form I" refers to Form I of compound (R)-2-[2-amino-3-(indol-3-yl)propionylamino]-2-methylpropionic acid, which is the form of compound (R)-2-[2-amino-3-(indol-3-yl)propionylamino]-2-methylpropionic acid isolated at room temperature or at a temperature higher than room temperature as described in Example 6, Example 11, and as previously characterized in U.S. Patent Application Publication No. 2006/0234947, which is incorporated herein by reference. In some embodiments, GAL-101 Form I refers to a stable form of GAL-101.

In some embodiments, the term "Form" as used in "GAL-101 Form I" or "GAL-101 Form II" refers to the polymorphs.

As used herein, "GAL-101 Form II" refers to Form II of compound (R)-2-[2-amino-3-(indol-3-yl)propionylamino]-2-methylpropionic acid, which is the form of (R)-2-[2-amino-3-(indol-3-yl)propionylamino]-2-methylpropionic acid isolated via a low temperature crystallization of GAL-101 Form I from water, e.g., at 0-5° C., as described herein in the examples of the invention. In some embodiments, GAL-101 Form II refers to the novel polymorph form of GAL-101. In some embodiments, GAL-101 Form II is not thermodynamically stable at above 25° C. In other embodiments, GAL-101 Form II refers to a metastable form of GAL-101.

GAL-101 Form II may be characterized by the FT-IR spectrum shown in FIG. 1 and/or the XPRD pattern shown in FIG. 2. In some embodiments, GAL-101 Form II is characterized by the single crystal X-ray diffraction pattern as described in Table 2 and Table 6 (Example 10).

The novel polymorph form (GAL-101 Form II) of the invention has a high water solubility (it dissolves in about 4 volumes of water at room temperature) and transforms to GAL-101 Form I, a stable form, very rapidly at above 30° C. In some embodiments, Form II of the compound converts gradually to Form I even in dry state at about 30-35° C.

In some embodiments, the novel polymorph GAL-101 Form II of the invention is at least 2 times as soluble in water as GAL-101 Form I. In some embodiments, the novel polymorph GAL-101 Form II of the invention is at least 5 times as soluble in water as GAL-101 Form I. In some embodiments, the novel polymorph GAL-101 Form II of the invention is at least 10 times as soluble in water as GAL-101 Form I. In some embodiments, the novel polymorph Form II of the invention is at least 15 times as soluble in water as GAL-101 Form I. In some embodiments, the novel polymorph Form II of the invention is at least 20 times as soluble in water as GAL-101 Form I.

In some embodiments, the solubility of the novel polymorph form (GAL-101 Form II) in water is greater than the solubility of GAL-101 Form I. This was very surprising and unexpected, since the stable Form I is almost insoluble in water.

GAL-101 Form II is highly crystalline and strongly oriented (it forms large plates).

As used herein, "ultrapure GAL-101 Form I" refers to a GAL-101 Form I that has a purity of from about 99.70 area % to about 99.999 area % by IPC-HPLC. In some embodiments, "ultrapure GAL-101" refers to a GAL-101 Form I or Form II that has a purity of from about 99.70% to about 99.999%.

As used herein, in some embodiments, the "compound" refers to (R)-2-[2-Amino-3-(indol-3-yl)propionylamino]-2-methylpropionic acid.

As used herein, the term "polymorph" refers to a solid phase of a substance which occurs in distinct forms due to different arrangements of molecules in a crystal lattice. The term polymorph includes crystalline forms as well as hydrates and solvates of such forms.

The present invention further provides a process for preparing Form II of compound (R)-2-[2-amino-3-(indol-3-yl)propionylamino]-2-methylpropionic acid (GAL-101 Form II) of the invention, comprising
  (a) mixing compound (R)-2-[2-amino-3-(indol-3-yl)propionylamino]-2-methylpropionic acid with an aqueous HCl to provide a solution of the compound;
  (b) cooling the solution to about 0-5° C., followed by adjusting the pH of the solution to about 5.6 with a base;
  (c) stirring the solution at about 0-5° C. until precipitation is complete; and
  (d) isolating the resulting precipitate to give the GAL-101 Form II.

In some embodiments, the aqueous HCl of step (a) has a concentration of from about 3 M to about 6 M, for example, about 3 M, about 3.5 M, about 4.0 M, about 4.5 M, about 5.0 M, about 5.5 M, and about 6.0 M. In other embodiments, the aqueous HCl of step (a) has a concentration of from about 5 M to about 6 M. In one embodiment, the aqueous HCl of step (a) has a concentration of about 5 M. In another embodiment, the aqueous HCl of step (a) has a concentration of about 5.5 M. In one embodiment, the aqueous HCl of step (a) has a concentration of about 6 M.

In some embodiments, the aqueous HCl of step (a) has a pH value of from about 3.0 to about 3.5. In other embodiments, the aqueous HCl of step (a) has a pH value of about 3.0. In some embodiments, the aqueous HCl of step (a) has a pH value of about 3.5.

In some embodiments, the amount of compound (R)-2-[2-amino-3-(indol-3-yl)propionylamino]-2-methylpropionic acid and the aqueous HCl of step (a) is in a ratio of about 1:3 (w/w). In some embodiments, the amount of compound (R)-2-[2-amino-3-(indol-3-yl)propionylamino]-2-methylpropionic acid and the aqueous HCl of step (a) is in a ratio of about 1:3.5 (w/w). In some embodiments, the amount of compound (R)-2-[2-amino-3-(indol-3-yl)propionylamino]-2-methylpropionic acid and the aqueous HCl of step (a) is in a ratio of about 1:4 (w/w). In some embodiments, the amount of compound (R)-2-[2-amino-3-(indol-3-yl)propionylamino]-2-methylpropionic acid and the aqueous HCl of step (a) is in a ratio of about 1:2.5 (w/w). In some embodiments, the amount of compound (R)-2-[2-amino-3-(indol-3-yl)propionylamino]-2-methylpropionic acid and the aqueous HCl of step (a) is in a ratio of about 1:2 (w/w).

In some embodiments, the mixing of step (a) is conducted at room temperature. In some embodiments, the mixing of step (a) is conducted at 0-5° C. In some embodiments, the mixing of step (a) is conducted at 5-10° C. In some embodiments, the mixing of step (a) is conducted at a temperature of below 0° C.

In some embodiments, the base of step (b) is a NaOH solution. In certain embodiments, the NaOH solution is a 20% NaOH aqueous solution.

In some embodiments, the pH of the solution of step (b) is adjusted while the temperature is maintained at about 0-5° C. In some embodiments, the pH of the solution of step (b) is adjusted while the temperature is maintained at about 5-10° C.

In some embodiments, the solution of step (c) is stirred overnight. In some embodiments, the solution of step (c) is stirred overnight at about 0-5° C. In some embodiments, the solution of step (c) is stirred overnight at about 5-10° C.

In some embodiments, the resulting precipitate of step (d) is isolated by filtration. In some embodiments, the resulting precipitate of step (d) is isolated by filtration on pre-chilled funnel.

In some embodiments, the process of the invention further comprises a step of drying the isolated precipitate at 0-5° C. by a drying agent. The drying agent can be any drying agents known in the art. In some embodiments, the drying agent is $P_2O_5$.

In some embodiments, in the process of the invention, compound (R)-2-[2-amino-3-(indol-3-yl)propionylamino]-2-methylpropionic acid of step (a) can be any form of the compound (e.g., GAL-101 Form I, or another form of the compound), or a mixture of any form of the compound available. In some embodiments, compound (R)-2-[2-amino-3-(indol-3-yl)propionylamino]-2-methylpropionic acid of step (a) is GAL-101 Form I, wherein said GAL-101 Form I is characterized by an X-ray powder diffraction pattern displaying peaks at ° 2θ (d value Å) angles 6.75 (13.095), 10.19 (8.678), 11.76 (7.524), 13.56 (6.531), 17.68 (5.017), 18.63 (4.764), 20.15 (4.407), 22.08 (4.026). In some embodiments, compound (R)-2-[2-amino-3-(indol-3-yl)propionylamino]-2-methylpropionic acid of step (a) is a mixture of GAL-101 Form I and GAL-101 Form II. In some embodiments, the mixture contains a small amount of GAL-101 Form II in addition to GAL-101 Form I.

In another aspect, the present invention provides Form II of compound (R)-2-[2-amino-3-(indol-3-yl)propionylamino]-2-methylpropionic acid (GAL-101 Form II) as prepared by the processes as described anywhere herein.

It is another aspect of the invention that the novel polymorph form, GAL-101 Form II, of the invention can be used to purify other polymorph forms of the compound, for example, GAL-101 Form I.

The present invention provides a method of preparing ultrapure Form I of compound (R)-2-[2-amino-3-(indol-3-yl)propionylamino]-2-methylpropionic acid (ultrapure GAL-101 Form I), characterized by an X-ray powder diffraction pattern displaying peaks at °2θ (d value Å) angles 6.75 (13.095), 10.19 (8.678), 11.76 (7.524), 13.56 (6.531), 17.68 (5.017), 18.63 (4.764), 20.15 (4.407), 22.08 (4.026), wherein the purity of the ultrapure Form I of the compound is from about 99.70 area % to about 99.999 area % by IPC-HPLC, the method comprising
  (a) mixing GAL-101 Form II of the compound with water to prepare a solution of GAL-101 Form II of the compound;
  (b) heating the solution of GAL-101 Form II to about 30-35° C. and cooling to room temperature to produce a precipitate; and
  (c) isolating and washing the precipitate to give ultrapure GAL-101 Form I.

In some embodiments, the heating of step (b) lasts about 2 hours. In some embodiments, the method of the invention further comprises a step of drying at about 45-50° C. following the washing step (c).

The present invention further provides a method for preparing ultrapure GAL-101 Form I, characterized by an X-ray powder diffraction pattern displaying peaks at °2θ (d value Å) angles 6.75 (13.095), 10.19 (8.678), 11.76 (7.524), 13.56 (6.531), 17.68 (5.017), 18.63 (4.764), 20.15 (4.407), 22.08 (4.026), wherein said ultrapure GAL-101 Form I has a purity of from about 99.70 area % to about 99.999 area % by IPC-HPLC, the method comprising
  (a) mixing GAL-101 with an aqueous HCl to provide a solution of GAL-101;
  (b) cooling the solution to about 5-10° C., followed by adjusting the pH of the solution to about 5.6 with a base;
  (c) stirring the solution at about 0-5° C. until precipitation is complete;
  (d) isolating the resulting precipitate to obtain GAL-101 Form II;
  (e) mixing the GAL-101 Form II of step (d) with water to prepare a solution of GAL-101 Form II;
  (f) heating the solution of GAL-101 Form II of step (e) to about 30-35° C. and cooling to room temperature to produce a precipitate; and
  (g) isolating and washing the precipitate to give an ultrapure GAL-101 Form I; wherein the washing step is optionally repeated for two or three times; and
  (h) optionally repeating steps (a) to (g).

In some embodiments, the mixing of step (a) is at room temperature.

In some embodiments, the aqueous HCl of step (a) has a concentration of from about 3 M to about 6 M. In other embodiments, the aqueous HCl of step (a) has a concentration of from about 5 M to about 6 M.

In some embodiments, the aqueous HCl of step (a) has a pH value of from about 3.0 to about 3.5. In some embodiments, the aqueous HCl of step (a) has a pH value of about 3.0.

In some embodiments, the amount of GAL-101 and the aqueous HCl of step (a) is in a ratio of about 1:3 (w/w).

In some embodiments, the base of step (b) is a NaOH solution. In some embodiments, the NaOH solution is a 20% NaOH aqueous solution.

In some embodiments, the solution of step (c) is stirred overnight at about 0-5° C.

In some embodiments, the heating of step (f) lasts about 2 hours.

In some embodiments, the method of the invention further comprises a step of drying at about 45-50° C. following the washing step (g).

In some embodiments, the GAL-101 of step (a) is prepared by the steps comprising
  (a) reacting compound (2)

(d)

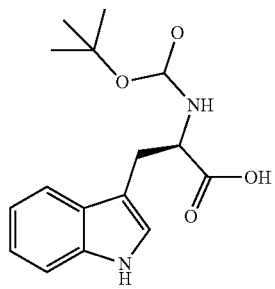

2 with tert-butyl-2-aminoisobutyrate (3) in the presence of 4-(4,6-dimethoxy-1,3,5-triazin-2-yl)-4-methylmorpholine chloride (DMTMM) to give compound (4)

ii.

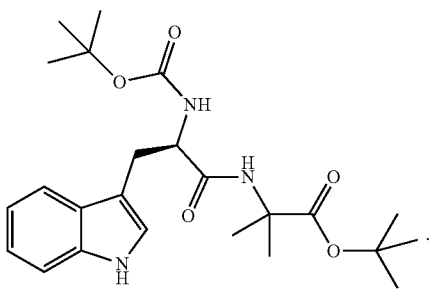

4

(b) removing the Boc groups from compound 4 with hydrogen chloride gas to give compound (5); and iii.

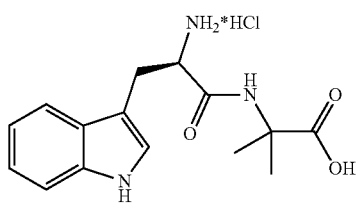

5

(c) providing a solution of compound (5) in water and adjusting the pH of the solution to about 5.5-5.7 to give GAL-101.

In some embodiments, the method of the invention optionally further comprises a step of purifying the GAL-101 from step (c) by (a) dissolving the GAL-101 in 5M HCl to provide a HCl solution of GAL-101 and filtering;

(b) adjusting the pH of the filtered solution to about 5.5-5.7 by 10% aqueous NaOH to give a precipitate;

(c) washing the precipitate with water and ethanol and dried.

The present invention further provides GAL-101 Form I prepared by the method as described herein. In some embodiments, methods described herein provide an ultrapure GAL-101 Form I.

The present invention also provides GAL-101 Form I having a purity of from about 99.70 area % to about 99.999 area % by IPC-HPLC. In some embodiments, GAL-101 Form I having a purity of from about 99.70 area % to about 99.999 area % by IPC-HPLC comprises an ultrapure GAL-101 Form I.

The present invention further provides a composition comprising ultrapure GAL-101 Form I as prepared by the method described herein and a pharmaceutically acceptable carrier or excipient. In some embodiments, the pharmaceutically acceptable carrier or excipient comprises hydroxypropylbetadex, citric acid, monohydrate, sodium citrate dihydrate, glycerol, and hypromellose.

The present invention further provides a formulation comprising ultrapure GAL-101 Form I, hydroxypropylbetadex, citric acid, monohydrate, sodium citrate dihydrate, glycerol, and hypromellose.

The present invention further provides a composition comprising GAL-101 Form II as prepared by the method described herein and a pharmaceutically acceptable carrier or excipient. In some embodiments, the pharmaceutically acceptable carrier or excipient comprises hydroxypropylbetadex, citric acid, monohydrate, sodium citrate dihydrate, glycerol, and hypromellose.

The present invention further provides a formulation comprising GAL-101 Form II, hydroxypropylbetadex, citric acid, monohydrate, sodium citrate dihydrate, glycerol, and hypromellose.

The present invention further provides a composition comprising ultrapure GAL-101 Form II as prepared by the method described herein and a pharmaceutically acceptable carrier or excipient. In some embodiments, the pharmaceutically acceptable carrier or excipient comprises hydroxypropylbetadex, citric acid, monohydrate, sodium citrate dihydrate, glycerol, and hypromellose.

The present invention further provides a formulation comprising ultrapure GAL-101 Form II, hydroxypropylbetadex, citric acid, monohydrate, sodium citrate dihydrate, glycerol, and hypromellose.

In some embodiments, a composition described herein further comprises thimerosal. In some embodiments, a formulation described herein further comprises thimerosal.

In a further aspect, the present invention provides a process for preparing Form II of (R)-2-[2-amino-3-(indol-3-yl)propionylamino]-2-methylpropionic acid of claim 1, comprising (a) reacting compound (2)

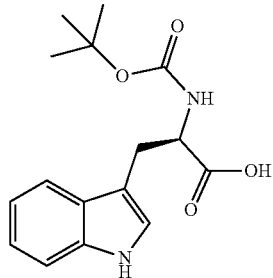

with tert-butyl-2-aminoisobutyrate (3) in the presence of 4-(4,6-dimethoxy-1,3,5-triazin-2-yl)-4-methylmorpholine chloride (DMTMM) to give compound (4)

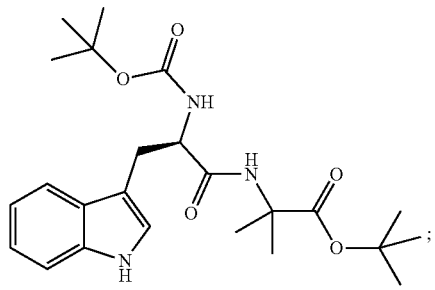

(b) removing the Boc group from compound (4) with hydrogen chloride gas to give compound (5);

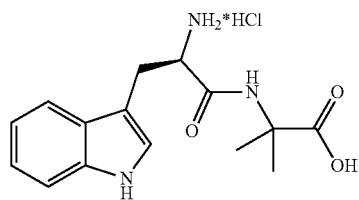

(c) providing a solution of compound (5) in water and adjusting the pH of the solution to about 5.5-5.7 to give a precipitate;

(d) mixing the precipitate from step (c) with an aqueous HCl to provide a solution;

(e) cooling the solution of step (d) to about 0-5° C., followed by adjusting the pH of the solution to about 5.6 with a 20% NaOH aqueous solution (f) stirring the solution at about 0-5° C. until precipitation is complete; and (g) isolating the resulting precipitate to give Form II of compound (R)-2-[2-amino-3-(indol-3-yl)propionylamino]-2-methylpropionic acid.

In some embodiments, the aqueous HCl of step (d) has a concentration of from about 3 M to about 6 M. In some embodiments, the aqueous HCl of step (d) has a pH value of from about 3.0 to about 3.5. In some embodiments, the aqueous HCl of step (d) has a pH value of about 3.0. In some embodiments, the solution of step (f) is stirred overnight. In some embodiments, the resulting precipitate of step (g) is isolated by filtration on pre-chilled funnel.

In some embodiments, the method of making Form II of the invention further comprises a step of drying the isolated precipitate of step (g) at 0-5° C. by a drying agent. In some embodiments, the drying agent is $P_2O_5$.

The present invention further provides a method of purifying Form I of compound (R)-2-[2-amino-3-(indol-3-yl)propionylamino]-2-methylpropionic acid (GAL-101 Form I), wherein said Form I of the compound is characterized by an X-ray powder diffraction pattern displaying peaks at °2θ (d value Å) angles 6.75 (13.095), 10.19 (8.678), 11.76 (7.524), 13.56 (6.531), 17.68 (5.017), 18.63 (4.764), 20.15 (4.407), 22.08 (4.026), comprising
  (a) mixing said GAL-101 Form I with an aqueous HCl to provide a solution of GAL-101 Form I;
  (b) cooling the solution to about 5-10° C., followed by adjusting the pH of the solution to about 5.6 with a base;
  (c) stirring the solution at about 0-5° C. until precipitation is complete;
  (d) isolating the resulting precipitate to obtain GAL-101 Form II;
  (e) mixing the GAL-101 Form II of step (d) with water to prepare a solution of Form II of the compound;
  (f) heating the solution of GAL-101 Form II of step (e) to about 30-35° C. and cooling to room temperature to produce a precipitate; and
  (g) isolating and washing the precipitate to give a pure GAL-101 Form I, wherein the washing step is optionally repeated for two or three times; and
  (h) optionally repeating steps (a) to (g);
wherein the purity of the pure GAL-101 Form I is from about 99.50 area % to about 99.95 area % by IPC-HPLC. In some embodiments, the pure GAL-101 Form I has a purity of from about 99.70 area % to about 99.999 area % by IPC-HPLC.

In some embodiments, GAL-101 Form I has a purity of from about 95.0 area % to about 99.0 area % by IPC-HPLC. In some embodiments, GAL-101 Form I has a purity of from about 95.0 area % to about 98.9 area % by IPC-HPLC. In some embodiments, GAL-101 Form I has a purity of from about 95.0 area % to about 98.5 area % by TPC-HPLC. In some embodiments, GAL-101 Form I has a purity of about 95.0 area %, about 95.5 area % by TPC-HPLC, about 96.0 area % by IPC-HPLC, about 96.5 area % by IPC-HPLC, about 97.0 area % by IPC-HPLC, about 97.5 area % by IPC-HPLC, 98.0 area % by TPC-HPLC, 98.5 area % by IPC-HPLC, 98.6 area % by TPC-HPLC, 98.7 area % by IPC-HPLC, 98.8 area % by IPC-HPLC, 98.9 area % by IPC-HPLC, or 99.0 area % by TPC-HPLC. In some embodiments, GAL-101 Form I has a purity of about 98.5 area % by IPC-HPLC.

In some embodiments, the amount of GAL-101 Form I is from 1.0 g to about 1000 g. In some embodiments, the amount of GAL-101 Form I is from 10 g to about 1000 g. In some embodiments, the amount of GAL-101 Form I is at least about 200 g. In some embodiments, the amount of GAL-101 Form I is at least about 300 g. In some embodiments, the amount of GAL-101 Form I is at least about 400 kg. In some embodiments, the amount of GAL-101 Form I is at least about 500 g. In some embodiments, the amount of GAL-101 Form I is at least about 600 g, at least about 700 g, at least about 800 g, at least about 900 g, or at least about 1000 g. In some embodiments, the amount of GAL-101 Form I is from 1.0 kg to about 100 kg. In some embodiments, the amount of GAL-101 Form I is from 10 kg to about 100 kg. In some embodiments, the amount of GAL-101 Form I is at least about 20 kg. In some embodiments, the amount of GAL-101 Form I is at least about 30 kg. In some embodiments, the amount of GAL-101 Form I is at least about 40 kg. In some embodiments, the amount of GAL-101 Form I is at least about 50 kg. In some embodiments, the amount of GAL-101 Form I is at least about 60 kg, at least about 70 kg, at least about 80 kg, at least about 90 kg, or at least about 100 kg. Accordingly, the method of the invention can be used for the purification of compound (R)-2-[2-amino-3-(indol-3-yl)propionylamino]-2-methylpropionic acid in large scales as well as in small scales.

In some embodiments, in the method of the invention, the mixing of step (a) is conducted at room temperature. In some embodiments, the mixing of step (a) is conducted at 0-5° C. In some embodiments, the mixing of step (a) is conducted at 5-10° C. In some embodiments, the mixing of step (a) is conducted at a temperature of below 0° C.

In some embodiments, in the method of the invention, the aqueous HCl of step (a) has a concentration of from about 3 M to about 6 M, for example, about 3 M, about 3.5 M, about 4.0 V, about 4.5 M, about 5.0 M, about 5.5 M, and about 6.0 M. In other embodiments, the aqueous HCl of step (a) has a concentration of from about 5 M to about 6 M. In one embodiment, the aqueous HCl of step (a) has a concentration of about 5 M. In another embodiment, the aqueous HCl of step (a) has a concentration of about 5.5 M. In one embodiment, the aqueous HCl of step (a) has a concentration of about 6 M.

In some embodiments, in the method of the invention, the aqueous HCl of step (a) has a pH value of from about 3.0 to about 3.5. In other embodiments, the aqueous HCl of step (a) has a pH value of about 3.0. In some embodiments, the aqueous HCl of step (a) has a pH value of about 3.5.

In some embodiments, in the method of the invention, the amount of compound (R)-2-[2-amino-3-(indol-3-yl)propionylamino]-2-methylpropionic acid and the aqueous HCl of step (a) is in a ratio of about 1:3 (w/w). In some embodiments, the amount of compound (R)-2-[2-amino-3-(indol-3-yl)propionylamino]-2-methylpropionic acid and the aqueous HCl of step (a) is in a ratio of about 1:3.5 (w/w). In some embodiments, the amount of compound (R)-2-[2-amino-3-(indol-3-yl)propionylamino]-2-methylpropionic acid and the aqueous HCl of step (a) is in a ratio of about 1:4 (w/w). In some embodiments, the amount of compound (R)-2-[2-amino-3-(indol-3-yl)propionylamino]-2-methylpropionic acid and the aqueous HCl of step (a) is in a ratio of about 1:2.5 (w/w). In some embodiments, the amount of compound (R)-2-[2-amino-3-(indol-3-yl)propionylamino]-2-methylpropionic acid and the aqueous HCl of step (a) is in a ratio of about 1:2 (w/w).

In some embodiments, in the method of the invention, the base of step (b) is a NaOH solution. In certain embodiments, the NaOH solution is a 20% NaOH aqueous solution.

In some embodiments, in the method of the invention, the pH of the solution of step (b) is adjusted while the temperature is maintained at about 5-10° C. In some embodiments, the pH of the solution of step (b) is adjusted while the temperature is maintained at about 0-5° C. In some embodiments, the pH of the solution of step (b) is adjusted while the temperature is maintained at about 0° C.

In some embodiments, in the method of the invention, the solution of step (c) is stirred overnight. In some embodiments, the solution of step (c) is stirred overnight at about 0-5° C. In some embodiments, the solution of step (c) is stirred overnight at about 5-10° C. In some embodiments, the solution of step (c) is stirred overnight below 0° C.

In some embodiments, in the method of the invention, the heating of step (f) lasts from about 1 hour to about 4 hours, for example 1 hour, 2 hours, 3 hours, or 4 hours. In some embodiments, in the method of the invention, the heating of step (f) lasts more than 4 hours. In some embodiments, in the method of the invention, the heating of step (f) lasts about 2 hours.

In some embodiments, the precipitate of step (g) is washed twice or three times with water. In some embodiments, the washing step of step (g) is repeated once. Thus, the precipitate of step (g) is washed twice. In other embodiments, the washing step of step (g) is repeated twice or more. Thus, the precipitate of step (g) is washed twice, three times, four times, or more until a desirable purity of the isolated precipitated is obtained.

In some embodiments, in the method of the invention, steps (a) to (g) are repeated once. For example, the obtained pure GAL-101 Form I of step (g) is purified in a second time by the method of the invention, including steps (a) to (g), to provide a purer GAL-101 Form I of the compound. In other embodiments, in the method of the invention, steps (a) to (g) are repeated twice. For example, the obtained pure GAL-101 Form I of step (g) from a second time is purified in a third time by the method of the invention, including a first steps (a) to (g) and a second steps (a) to (g), to provide a much purer GAL-101 Form I of the compound. In certain embodiments, steps (a) to (g) are repeated multiple times until a desirable purity of GAL-101 Form I is obtained.

In some embodiments, the method of the invention further comprises a step of testing the solubility of the precipitate prior to step (g).

In some embodiments, in the method of the invention, the obtained pure GAL-101 Form I has a purity of from about 99.0 area % to about 99.9 area % by IPC-HPLC. In some embodiments, the obtained pure GAL-101 Form I has a purity of from about 99.50 area % to about 99.99 area % by IPC-HPLC. In other embodiments, the obtained pure GAL-101 Form I has a purity of about 99.00 area % by HPLC, about 99.10 area % by HPLC, about 99.20 area % by HPLC, about 99.30 area % by HPLC, about 99.40 area % by HPLC, about 99.50 area % by HPLC, about 99.60 area % by HPLC, about 99.70 area % by HPLC, about 99.80 area % by HPLC, or about 99.90 area % by HPLC, or above 99.99 area % by HPLC.

In some embodiments, the obtained pure GAL-101 Form I has a purity as described in the examples herein. In some embodiments, the obtained pure GAL-101 Form I has a purity of about 99.80 area % by HPLC as described in Example 7.

In some embodiments, the method of the invention further comprises a step of drying at about 45-50° C. following the washing step (g).

In another aspect, the present invention provides a method of purifying a Form I of compound (R)-2-[2-amino-3-(indol-3-yl)propionylamino]-2-methylpropionic acid (GAL-101 Form I), comprising purifying the isolated pure GAL-101 Form I of step (g) through the steps of (a)-(g) in a second time to produce a GAL-101 Form I having a higher purity than the prior isolated GAL-101 Form I without the second time of purification.

The method of the invention to purify a GAL-101 Form I is an efficient method to remove and reduce the impurities of compound (R)-2-[2-amino-3-(indol-3-yl)propionylamino]-2-methylpropionic acid. In some embodiments, in the method of the invention, the isolation of GAL-101 Form II of the invention is needed. In other embodiments, in the method of the invention, the isolation of GAL-101 Form II is not necessary. In some embodiments, after purification by the method of the invention, the purity of GAL-101 Form I is increased to about 99.50 area % by HPLC, to about 99.60 area % by HPLC, to about 99.70 area % by HPLC, to about 99.80 area % by HPLC, or to about 99.90 area % by HPLC, or to a purify of above 99.99 area % by HPLC. In some embodiments, GAL-101 Form II has a purity of about 99.50 to about 99.60, to about 99.70, to about 99.80, or to about 99.90, or to a purify of above 99.99.

In some embodiments, in the method of the invention, the optimal temperature of the isolation of GAL-101 Form II of the compound is about 0-5° C.

In some embodiments, in the method of the invention, the complete transformation of GAL-101 Form II of the compound to GAL-101 Form I is observed at room temperature (20-25° C.) within 15 minutes.

At a higher temperature (e.g., 40-50° C.) significant degradation of the product is observed. Further, the isolated yield (45%-50% instead of 60%) and the efficiency of the purification are slightly lower (98.9 area %) at −5° C. than at 0-5° C. The cause of these results could be the freezing of water and impurities from the reaction mixture at −5° C., as shown in Table 4. During the filtration step, the thick suspension could be warmed up and partly dissolves Form II of the compound and decreases the yield.

TABLE 4

| Temperature | Purity | Yield | Form |
|---|---|---|---|
| −5° C. | 98.9 area % | 45-50% | metastable |
| 0-+5° C. | 99.5 area % | 60% | metastable |
| 10-25° C. | no data available | no data available | mixture |
| 30-40° C. | 98.5-98.7 area % | 75-78% | stable |

The complete transition from GAL-101 Form II to GAL-101 Form I is detected at room temperature (20-25° C.) within 15 minutes. The transition can start at above 10° C. The transition can be followed by microscope, the large metastable crystals transform to small crystals within a few minutes at ambient temperature (FIGS. 6-14).

As used herein, in some embodiments, the term "transition" refers to the transformation from polymorph GAL-101 Form II to polymorph GAL-101 Form I of the compound.

It is another aspect of the invention that the method of the invention can be used to prepare Form I of (R)-2-[2-amino-3-(indol-3-yl)propionylamino]-2-methylpropionic acid (GAL-101 Form I) with a much higher purity than other known methods. In some embodiments, the invention provides GAL-101 Form I as prepared by the method of the invention.

In another aspect, the present invention provides Form I of (R)-2-[2-amino-3-(indol-3-yl)propionylamino]-2-methylpropionic acid (GAL-101 Form I) having a purity of from about 99.50 area % to about 99.99 area % by IPC-HPLC. In some embodiments, GAL-101 Form I has a purity of about 99.0 area % by HPLC, about 99.10 area % by HPLC, about 99.20 area % by HPLC, about 99.30 area % by HPLC, about 99.40 area % by HPLC, about 99.50 area % by HPLC, about 99.60 area % by HPLC, about 99.70 area % by HPLC, about 99.80 area % by HPLC, or about 99.90 area % by HPLC, or above 99.99 area % by HPLC.

The term "about" or "approximately" usually means within 20%, alternatively within 10%, including within 5% of a given value or range. Alternatively, especially in biological systems, the term "about" means within about a log (i.e., an order of magnitude), including within a factor of two of a given value.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments described may be presented in a range format. It should be understood that the description in range format is merely for convenience and brevity and should not be construed as an inflexible limitation on the scope of for example, but not limited to percent of a therapeutically effective dose. Accordingly, the description of a range should be considered to have specifically disclosed all the possible sub ranges as well as individual numerical values within that range. For example, description of a range such as from 1 to 6 should be considered to have specifically disclosed sub ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

In one embodiment, a "pharmaceutical composition" refers to a preparation of GAL-101 as described herein with other chemical components such as physiologically suitable carriers and excipients. The purpose of a pharmaceutical composition is to facilitate administration of a compound to an organism. In certain embodiments, a "pharmaceutical composition" provides the pharmaceutical dosage form of a drug. "Pharmaceutical compositions" in certain embodiments include any known dosage form in the art. As used herein, the terms "pharmaceutical composition" or "composition" or "formulation" may be used interchangeably having all the same meanings and qualities.

The compositions may be employed as solids, such as coated or uncoated tablets or filled capsules; or liquids, such as solutions, suspensions, emulsions, or capsules filled with the same; or may be employed as aerosols, such as a spray or mists. The compositions can be prepared for oral use. They can be in the form of suppositories or capsules for rectal administration. In some embodiments, compositions are prepared for nasal use, for example a nasal spray or mist. In some embodiments, compositions are prepared for use in the eye in the form of eye-drops or as a sterile injectable solution for intra-ocular administering. In some embodiments, compositions are prepared for systemic use in the form of an injectable solution, for example but not limited to, for intrathecal, subcutaneous, implanted slow-release depots, direct injection using an in-dwelling catheter, intramuscular, or intravenous injection. In some embodiments, compositions are prepared for systemic or local use in the form of a topical ointment, a patch, or a dermal patch.

Compositions can be in the form of sterile injectable solutions for parenteral (including intrathecal, subcutaneous, intramuscular, direct injection using an in-dwelling catheter, implanted slow release depots, or intravenous injection) use. They can be in liquid or semi-liquid form for ophthalmic application to the eye (including eye-drops or intra-ocular injection). In some embodiments, ophthalmic application to the eye uses a composition in the form of eye drops, eye creams, and intraocular depot formulations. In some embodiments, compositions are in the form of nose sprays or mists for treatment of ophthalmic conditions. In some embodiments, compositions are in the form of nose sprays or mists for treatment of neurological conditions.

Such pharmaceutical compositions and unit dosage forms thereof may comprise conventional or new ingredients in conventional or special proportions, with or without additional active compounds. Such unit dosage forms may contain any suitable effective amount of GAL-101 commensurate with the intended dosage range to be employed.

In some embodiments, compositions containing 0.5 to 1000 milligrams, preferably 1 to 100 milligrams of active ingredient per application unit are suitable representative unit dosage forms. In some embodiments, compositions containing about 0.01-10 mg/kg bodyweight on peroral administration and 0.001-10 mg/kg bodyweight on parenteral administration.

In one embodiment, as used herein, the term "excipient" applied to pharmaceutical compositions for the method disclosed herein refers to a diluent, adjuvant, or carrier with which GAL-101 is administered. Such pharmaceutical excipients often are sterile liquids, such as water or saline solutions. Other excipients, depending on the type of administration, can be aqueous dextrose solutions, aqueous glycerol solutions, and oils, including those of animal, vegetable or synthetic origin (see Remington and AR Gennaro, 20th Edition, (2000) "Remington: The Science and Practice of Pharmacy", published by Lippincott, Williams, and Wilkins.).

For ophthalmological applications (for ocular diseases and disorders), topic formulations are often applied. They are often water-based solutions or dispersions. However, water-free solutions or suspensions could also be used.

It is another aspect of the present invention that the composition comprising GAL-101 can be prepared in liquid or semi-liquid form for ophthalmic application to the eye (including eye-drops or intra-ocular injection). In some embodiments, ophthalmic application to the eye uses a composition in the form of eye drops, eye creams, and intraocular depot formulations. In some embodiments, compositions are in the form of nose sprays or mists for treatment of ophthalmic conditions. In some embodiments, compositions are in the form of nose sprays or mists for treatment of neurological conditions. In some embodiments, such formulations of the invention may comprise ultra-pure GAL-101 Form I. In some embodiments, the formulations of the invention may be made directly from ultra-pure GAL-101 Form II. In other embodiments, the formulations of the invention can be used as claimed in other applications that are for the use of GAL-101.

In some embodiments, the formulation of the invention comprises the ingredients as recited in Table 5:

TABLE 5

Formulation of ultrapure GAL-101.

| Position | Component | Amount (mg) | Quality | Function |
|---|---|---|---|---|
| 1 | GAL-101 | 20.00 | In house specification | Active Pharmaceutical ingredient |
| 2 | Hydroxypropyl-betadex | 110.00 | Ph. Eur. | Solubilizer |
| 3 | Citric acid, monohydrate | 0.87 | Ph. Eur. | Buffer agent |
| 4 | Sodium citrate dihydrate | 10.60 | Ph. Eur. | Buffer agent |

TABLE 5-continued

Formulation of ultrapure GAL-101.

| Position | Component | Amount (mg) | Quality | Function |
|---|---|---|---|---|
| 5 | Glycerol | 5.00 | Ph. Eur. | Isotonicity agent |
| 6 | Hypromellose | 5.00 | Ph. Eur. | Viscosity modifier |
| 7 | Water for injection | 896.49 | Ph. Eur. | Solvent |

As disclosed herein, the dose of the components in the compositions for a method of use disclosed herein is determined to ensure that the dose administered continuously or intermittently will not exceed an amount determined after consideration of the results in test animals and the individual conditions of a patient. A specific dose naturally varies depending on the dosage procedure, the conditions of a patient or a subject animal such as age, body weight, sex, sensitivity, feed, dosage period, drugs used in combination, seriousness of the disease. The appropriate dose and dosing times under certain conditions can be determined by the test based on the above-described indices but may be refined and ultimately decided according to the judgment of the practitioner and each patient's circumstances (age, general condition, severity of symptoms, sex, etc.) according to standard clinical techniques.

Toxicity and therapeutic efficacy of the compositions for the method disclosed herein can be determined by standard pharmaceutical procedures in experimental animals, e.g., by determining the $LD_{50}$ (the dose lethal to 50% of the population) and the $ED_{50}$ (the dose therapeutically effective in 50% of the population). The dose ratio between therapeutic and toxic effects is the therapeutic index and it may be expressed as the ratio $ED_{50}/LD_{50}$. Those pharmaceutical compositions that exhibit large therapeutic indices are preferred.

In some embodiments, each dose used in a method described herein comprises 100% of the therapeutically effective dose. In some embodiments, each dose used in a method described herein comprises 20-75% of the therapeutically effective dose. In some embodiments, each dose used in a method described herein comprises 20, 25, 30, 35, 40, 45, 50, 55, 60, 65, 70, or 75% of the therapeutically effective dose.

In some embodiments, individual doses of multiple doses to be administered each comprise 100% of the therapeutically effective dose, or 75-100% of the therapeutically effective dose, or 20-75% of the therapeutically effective dose, or any combination thereof.

In some embodiments, ultrapure GAL-101 and pharmaceutical compositions thereof, may be used in methods to treat, prevent, or reverse Aβ functional toxicity of neuronal, non-neuronal, and neuro-sensory cells in a subject in need. Methods treating, preventing, or reversing Aβ functional toxicity may in some embodiments, provide symptomatic treatment, thereby improving a function or functions in the subject in need. In some embodiments, the improved function comprises a function damaged, reduced, inhibited, or altered in an amyloid β-associated disease or condition.

Methods treating, preventing, or reversing amyloid β functional toxicity, in some embodiments comprise a step administering ultrapure GAL-101 or a pharmaceutical composition thereof. In some embodiments, treating, preventing, or reversing amyloid β functional toxicity, comprises a step of administering ultrapure GAL-101 or a formulation thereof.

In some embodiments, disclosed herein are methods of treating, preventing, slowing the progress of, halting the progress of an amyloid β diseases or conditions, said method comprising administering an ultrapure GAL-101 or a pharmaceutical composition thereof. In some embodiments, disclosed herein are methods of treating, preventing, slowing the progress of, halting the progress of an amyloid β diseases or conditions, said method comprising administering an ultrapure GAL-101 or a formulation thereof.

In some embodiments, a method of use disclosed herein comprises administering an ultrapure GAL-101 or a pharmaceutical composition thereof, or a formulation thereof, as disclosed herein, in a pattern of dosage within a time period. In some embodiments, the administration may be at regular intervals, or at irregular intervals, or a combination thereof. In some embodiments, the administration may be at regular intervals. In some embodiments, the administration may be at irregular intervals. Some embodiments of interval intermittent treatment are described in detail in publication WO 13/18960, which is incorporated herein in its entirety.

As used herein, the phrase "Intermittent interval administration" encompasses specific embodiments of interval administration wherein the second dose equals a percentage (%) of the first dose. The second period will often be a longer time period than the first period. For example, the first period may be one day, and the second period may be one or more weeks, or one or more months; or the first period will be one week, and the second period will be two or more weeks, or one or more months. Often, the second period will be less than or equal to a year. In some embodiments, the interval or a portion thereof, repeat themselves.

As used herein, the phrase "Continuous administration" or "non-interval" administration encompass regular administration of doses at equal time periods.

In some embodiments, an amyloid β ophthalmic disease or condition comprises primary angle-closure glaucoma, secondary open-angle glaucoma, wide-angle glaucoma, steroid-induced glaucoma, traumatic glaucoma, pigmentary dispersion syndrome, pseudo-exfoliation syndrome, secondary angle-closure glaucoma, neovascular glaucoma, early and intermediate dry (non-exudative) age-related macular degeneration, macular degeneration with geographic atrophy, exudative ("wet") macular degeneration, or diabetic retinopathy, or a combination thereof. In some embodiments, methods disclosed herein treating, preventing, slowing the progress of, halting the progression of, or reversing an amyloid β ophthalmic disease comprise improving or halting or slowing the loss of visual acuity, low luminescence vision, contrast sensitivity, cone contrast sensitivity, color vision, focal and general retinal light sensitivity in photopic mesopic (light adaptation) and scotopic (dark adaptation) conditions, and indirectly also postural stability, gait balance and mobility, in said subject.

When methods of use described herein are implemented in a subject suffering from all types of glaucoma, reversal, slowing of, or halting of amyloid β functional toxicity of retinal eye cells, for example RGC or RPE, may be measured using OCT, visual field exams, microperimetry, measurement of low luminance visual acuity, measurement of dark adaptation, and measurement of low luminance reading speed.

In some embodiments, an amyloid β neurological disease or condition comprises type II diabetes mellitus, Alzheimer's disease (AD), early onset Alzheimer's disease, late onset Alzheimer's disease, pre-symptomatic Alzheimer's disease, SAA amyloidosis, hereditary Icelandic syndrome, multiple myeloma, medullary carcinoma, aortic medical amyloid, Insulin injection amyloidosis, prion-systemic amyloidosis, chronic inflammation amyloidosis, senile systemic amyloidosis, pituitary gland amyloidosis, hereditary renal amyloidosis, familial British dementia, Finnish hereditary amyloidosis, familial non-neuropathic amyloidosis, and disorders and prion diseases, or a combination thereof.

In some embodiments, an amyloid β neurological disease or condition comprises diabetes mellitus. In some embodiments, an amyloid β neurological disease or condition comprises type II diabetes mellitus.

When the neurological disease comprises Alzheimer's disease (AD), early onset Alzheimer's disease, late onset Alzheimer's disease, or pre-symptomatic Alzheimer's disease, in some embodiments, methods disclosed herein provide slowing of the disease, halting the disease progress, or improvement of cognitive deficiencies, improvement memory loss, reduction of abnormal behavior, reduction of hallucinations, reduction of loss of spatial orientation, reduction of apraxia, reduction of aggression, improvement in the ability to perform activities of daily living, or other symptoms of dementia, or any combination thereof, in said subject.

It is to be understood that any use of any of the compounds as herein described may be used in the treatment of any disease, disorder or condition as described herein, and represents an embodiment of this invention. In one embodiment, the compounds are a free base, free acid, non-charged or non-complexed compound.

The following examples are presented in order to more fully illustrate the preferred embodiments of the invention. They should in no way, however, be construed as limiting the broad scope of the invention.

EXAMPLES

Example 1

Preparation of Form II of (R)-2-[2-Amino-3-(indol-3-yl)propionylamino]-2-methylpropionic Acid To a three necked 1 L flask equipped with stirrer and thermometer, 60.0 g (207.4 mmol) of (R)-2-[2-amino-3-(indol-3-yl)propionylamino]-2-methylpropionic acid, which is as synthesized by methods as described herein, e.g., at Examples 6 and 11, or by the method as previously described in U.S. Patent Application Publication No. 2006/0234947, was added to a mixture of 167.0 mL of water and 21.0 mL of concentrated hydrochloric acid, resulting in the formation of a yellowish brown solution. The pH of the solution was set to 5.6 with 53.0 mL of a 20% NaOH solution at 0-5° C. About 30 minutes later, the crystallization started at 0-5° C. The suspension was stirred overnight at 0-5° C. The suspension was filtered on a pre-chilled funnel. As an in-process control, the solubility of a part of the filter cake in water was checked. Immediately dissolving crystals indicated formation of form II. Form II of (R)-2-[2-Amino-3-(indol-3-yl)propionylamino]-2-methylpropionic acid was isolated and dried at 0-5° C. over $P_2O_5$.

Example 2

Characterization of Form II of (R)-2-[2-Amino-3-(indol-3-yl)propionylamino]-2-methylpropionic Acid by Infrared (IR) Spectroscopy The FT-IR spectra were measured with a BioRad (Digilab) FTS-60A spectrometer equipped with a $LN_2$-cooled MCT detector (4000-550 $cm^{-1}$) using a Golden Gate® Diamond ATR (internal reflection) accessory. To avoid eventual decomposition, the samples were used as neat substances slightly pressed to the surface of the diamond ATR optical element. The relative intensities of the obtained absorbance spectra were subsequently corrected using the "Advanced ATR correction" routine to obtain spectra corresponding to a normal transmission measurement.

In these measurements, the region between 2350-1850 $cm^{-1}$ may be distorted by strong diamond absorption, therefore this region is not evaluated (deleted from the spectra); however, for the examined compounds no characteristic absorption is expected in this region.

The FT-IR spectra of Forms I and II are shown in common wavenumber scale in FIG. 1. The spectra demonstrate that Forms I and II are distinct substances. The spectra show that Forms I and II are prevailingly present in zwitterionic form (very broad, strong absorption between 3200-2500 $cm^{-1}$ due to $NH_3^+$ groups, and strong absorption bands around 1550 and 1355 $cm^{-1}$ due to the carboxylate group).

The main visible differences in the spectra (a greater number of strong and very broad absorption bands, as in the 3450-3200 $cm^{-1}$ region and in the lower frequency part, 1700-600 $cm^{-1}$, and increased background absorption) are associated with a more extended H-bonded network formed in GAL-101 Form II, with participation of molecules of water incorporated in the crystal structure and involving even in the indole NH group. The latter NH group is essentially free in Form I (see the characteristic, sharp indole vNH band at 3426 $cm^{-1}$), but it broadens and gets shifted to 3371 $cm^{-1}$ in Form II. Form I does not contain water.

The amide carbonyls are also in different H-bonded states in the two substances. In Form II, it absorbs strongly at 1678 $cm^{-1}$ as a usual "amide I" band in an open chain peptide with trans orientation of C═O and N—H bonds, while in Form I it becomes much weaker and moves down to 1665 $cm^{-1}$, which may indicate twisting of the backbone of the substituent and participation of the amid carbonyl in an H-bond. It is not excluded that in this conformation the charged $NH_3^+$ and $CO_2^-$ groups may be engaged in intramolecular H-bond(s).

Example 3

Characterization of GAL-101 Form II by X-Ray Powder Diffraction

The crystal structure of Form I and Form II forms were determined by X-ray powder diffraction analysis by the Chemical Research Centre Laboratory of Powder in the Central Research Institute of Hungarian Academy of Sciences.

X-ray powder diffraction (XRPD) patterns were obtained in a Philips model PW 3710 based PW 1050 Bragg-Brentano parafocusing goniometer using CuKa radiation (l=0.15418 nm), graphite monochromator and proportional counter. The XRD scans were digitally recorded in the 2θ range of 3-35deg with a step size of 0.04deg.

Form II was measured at 20-25° C. (long dashed line), then heated at 30-35 for 15 minutes (solid line), then another 60 minutes (dotted line) (FIG. 2). Form I was also measured (short dashed line). According to the measurements, Form II is highly crystalline and strongly oriented (it forms large plates). GAL-101 Form II converts gradually to Form I, even in a dry state at 30-35° C.

Figure 3:
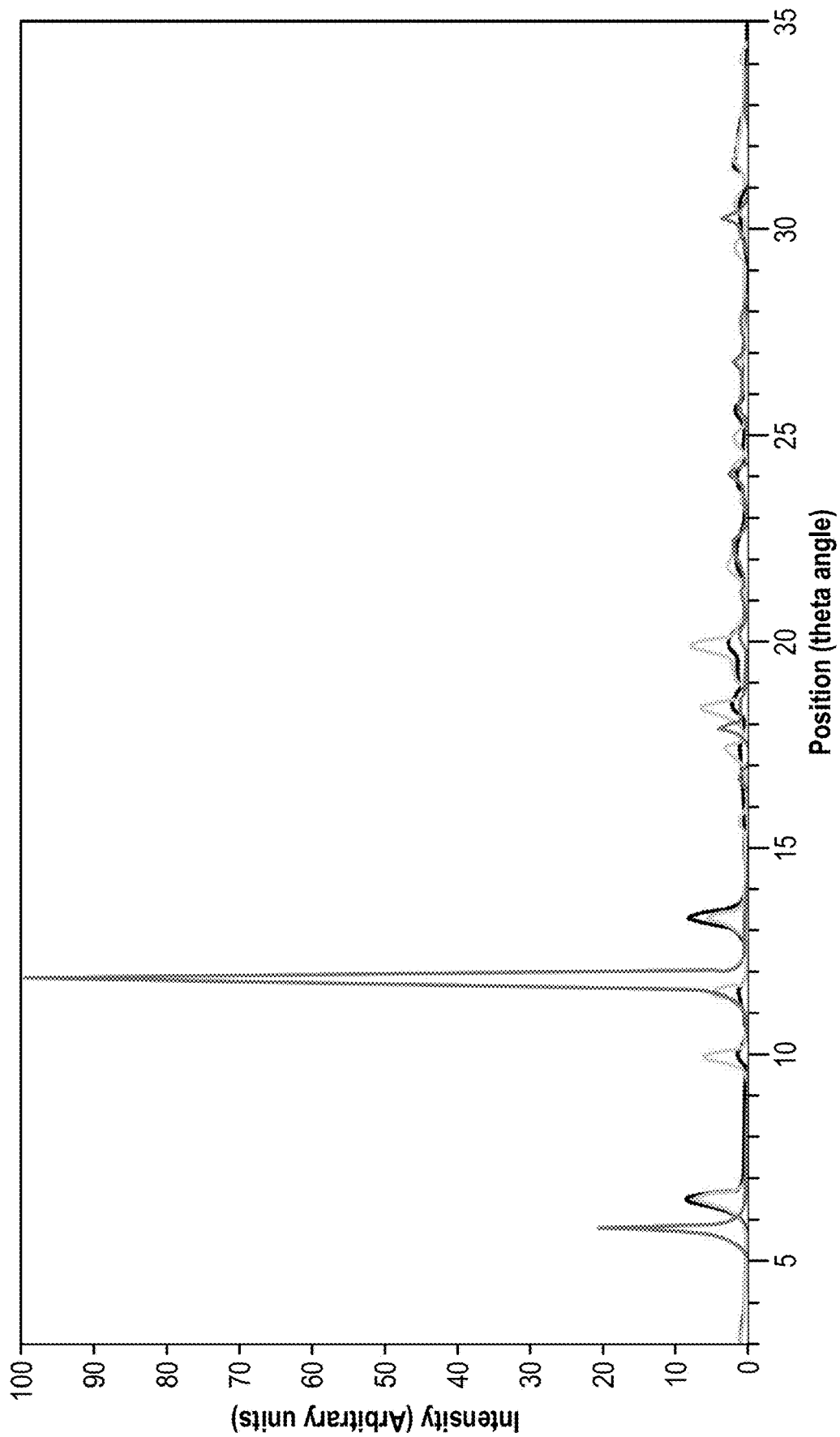
FIG. 3 shows an X-ray powder diffraction diagram (XPRD) demonstrating the transition of GAL-101 Form II (dark grey line) to GAL-101 Form I (black line) at 50-60° C. over a period of 30 minutes. Reference diffractogram of Form I is shown in light grey.

The transition of Form II (dark grey line) to Form I (black line) was complete at 50-60° C. within 30 minutes (FIG. 3). The reference diffractogram of Form I is shown in grey.

Figure 4:
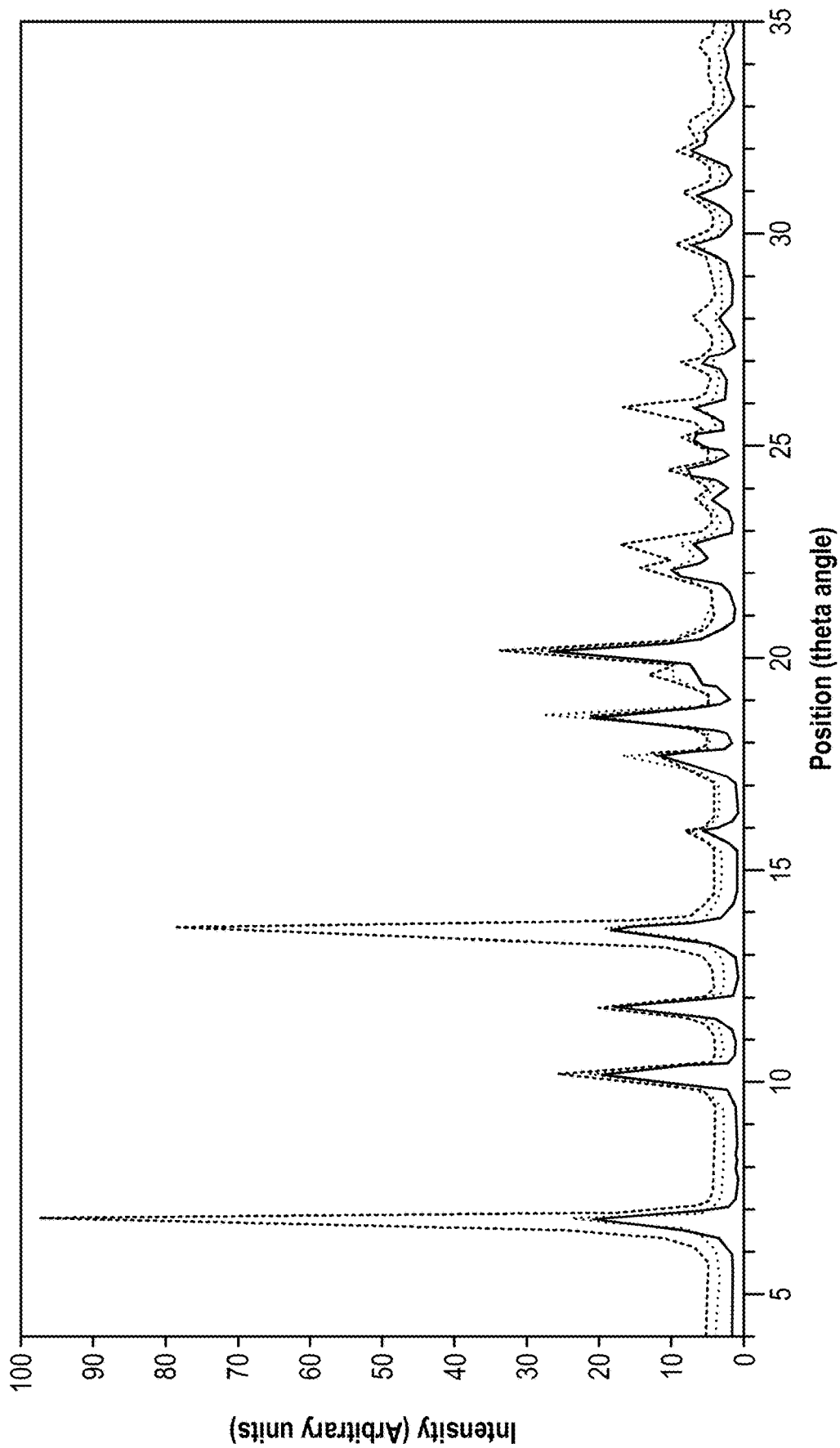
FIG. 4 shows a comparison XRPD for different batches of GAL-101 Form I.

Comparison of the XRPD of different batches of Form I (i.e., prepared in the laboratory (CT-1134.07, short dashed line), in the plant (2/1308/02/00859, dashed line) and newly prepared through transition from Form II (KP-0313.08, black line) showed the same crystalline form (FIG. 4).

Example 4

Characterization of Form II of (R)-2-[2-Amino-3-(indol-3-yl)propionylamino]-2-methylpropionic Acid by Thermogravimetric (TG) Analysis The thermoanalytical measurements were performed by a TA 2050 TG thermobalance and TA 2920 DSC cell (maker TA Instruments Company).

The following experimental parameters were used:
TG measurements
Sample weight 5-6 mg
Heating 5° C./min
Temperature range ambient –350° C.
Inertisation nitrogen, 10 l/h
DSC measurements
Sample weight 5-6 mg
Heating 5° C./min
Temperature range ambient –350° C.
Inertisation nitrogen, 10 l/h Prior to the measurements, the equipment was calibrated: TG balance—by indium metal and calcium oxalate monohydrate; DSC cell—indium metal.

The sample of Form I contained minimal adsorption moisture and no hydrate water.

Figure 5:
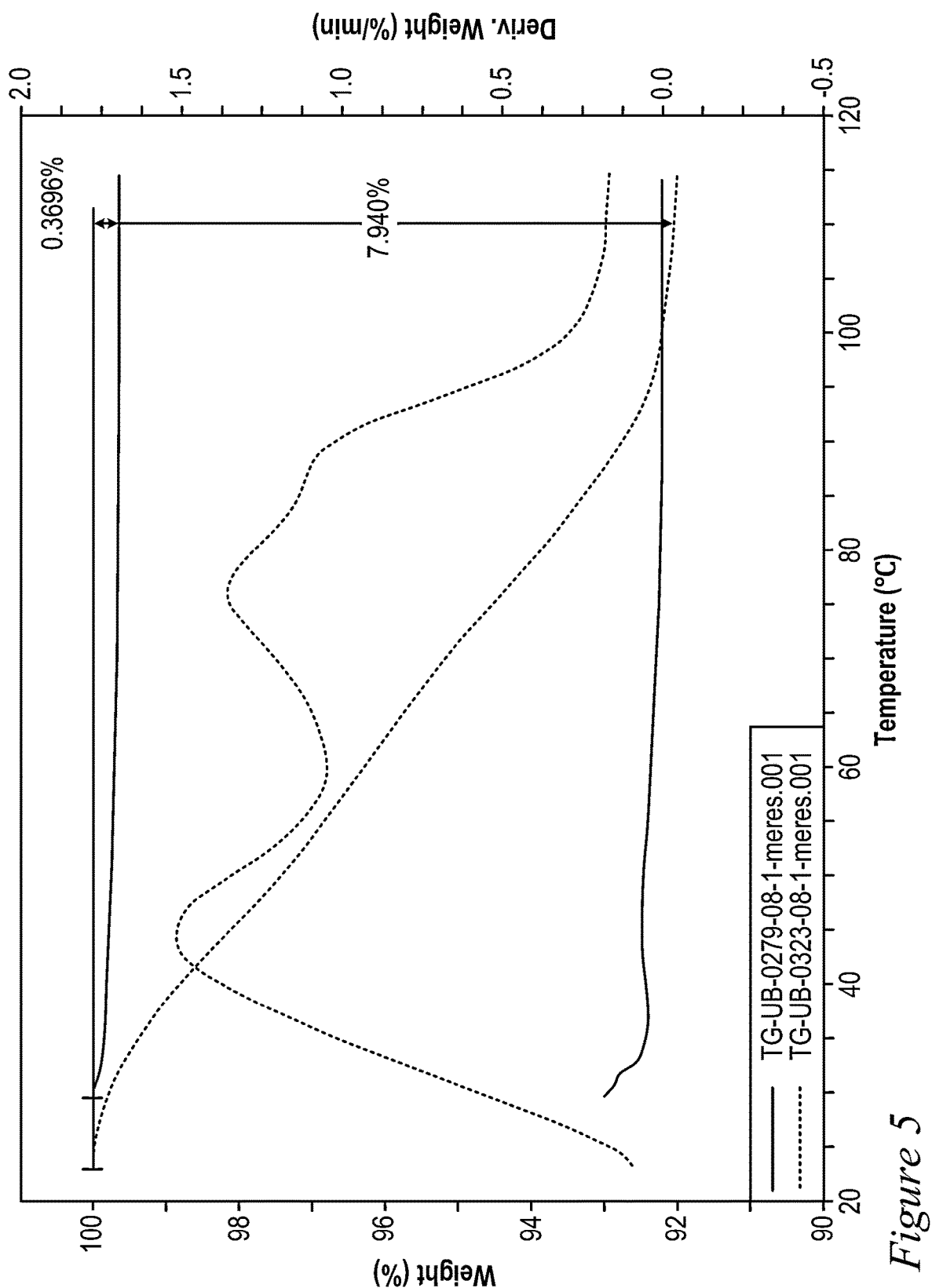
FIG. 5 shows a TG analysis for GAL-101 Form I (black) and GAL-101 Form II (dashed line).
Figure 6:
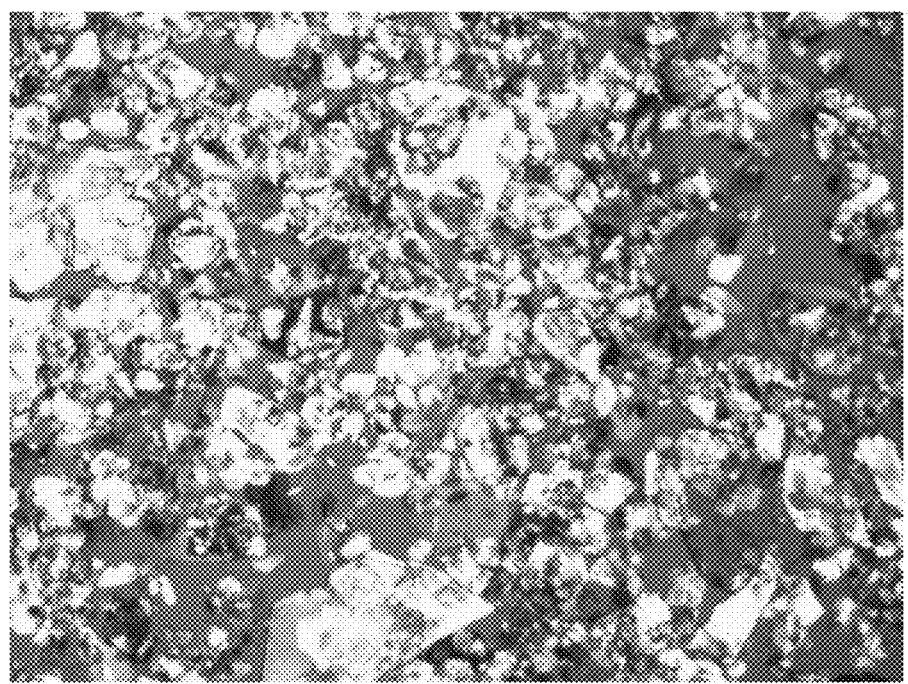
FIG. 6 shows the transition of wet GAL-101 Form II (kinetic stage 1 (T=0 second), initial Form II).
Figure 7:
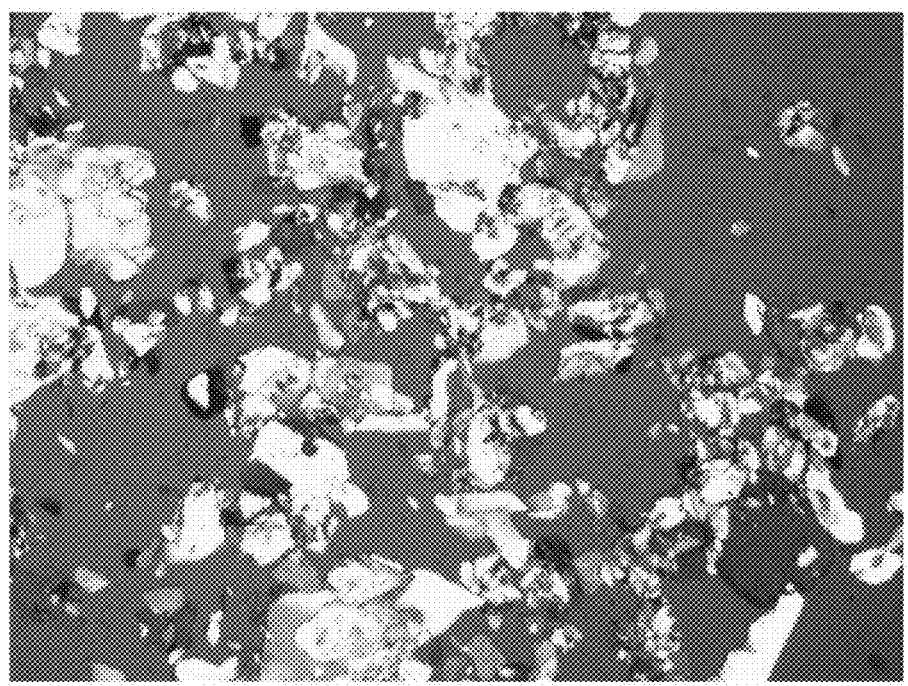
FIG. 7 shows the transition of wet GAL-101 Form II (kinetic stage 2(T=20 seconds), small crystals mostly dissolved).
Figure 8:
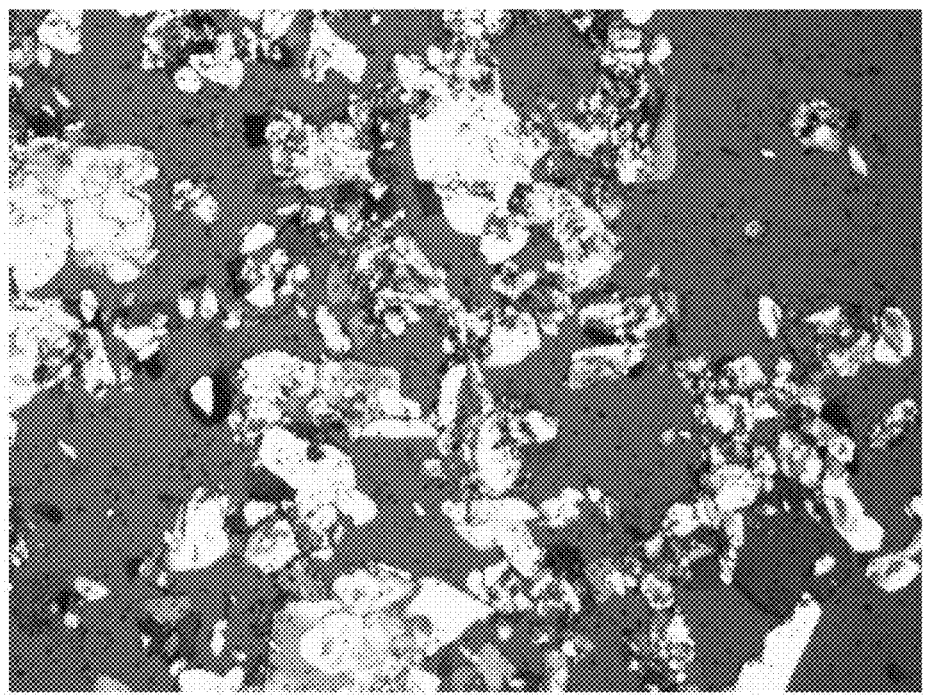
FIG. 8 shows the transition of wet GAL-101 Form II o (kinetic stage 3(T=60 seconds), the crystals of Form I appears in the liquid phase).
Figure 9:
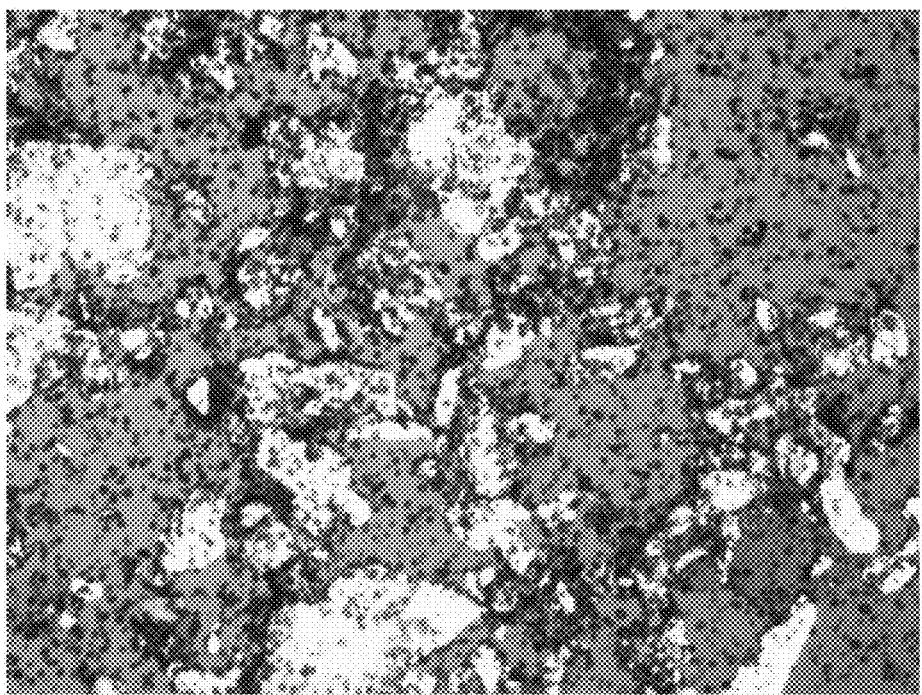
FIG. 9 shows the transition of wet GAL-101 Form II (kinetic stage 4 (T=80 seconds)).
Figure 10:
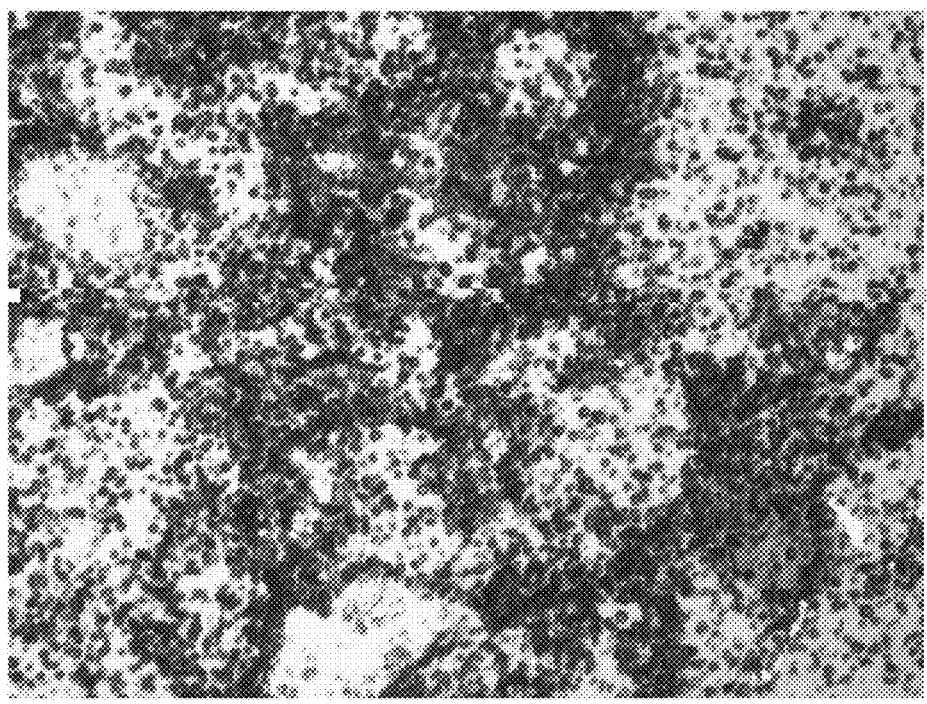
FIG. 10 shows the transition of wet Form II (kinetic stage 5 (T=120 seconds), most of the GAL-101 Form II transformed to Form I).
Figure 11:
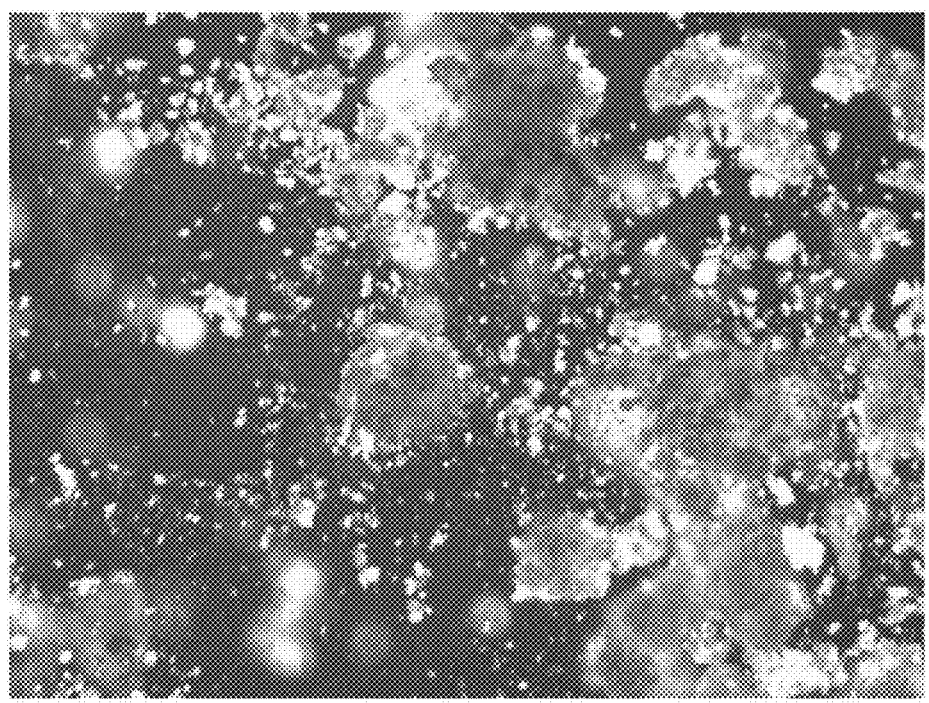
FIG. 11 shows the transition of dry GAL-101 Form II of (start).
Figure 12:
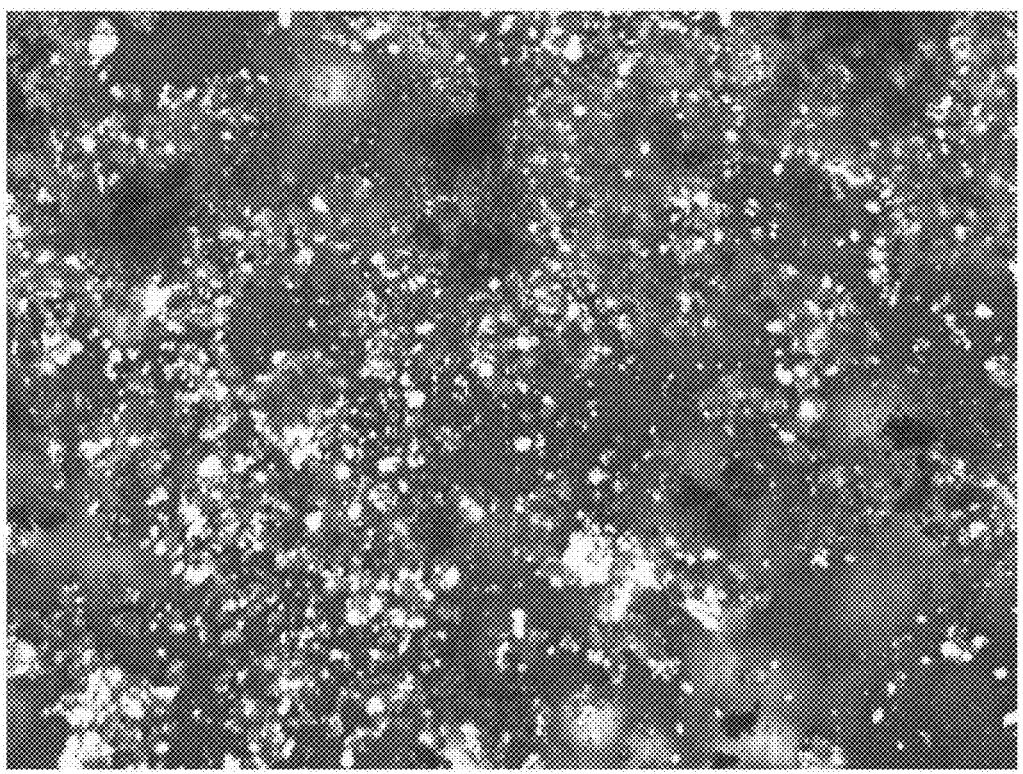
FIG. 12 shows the transition of dry GAL-101 Form II of (intermediate stage 1).
Figure 13:
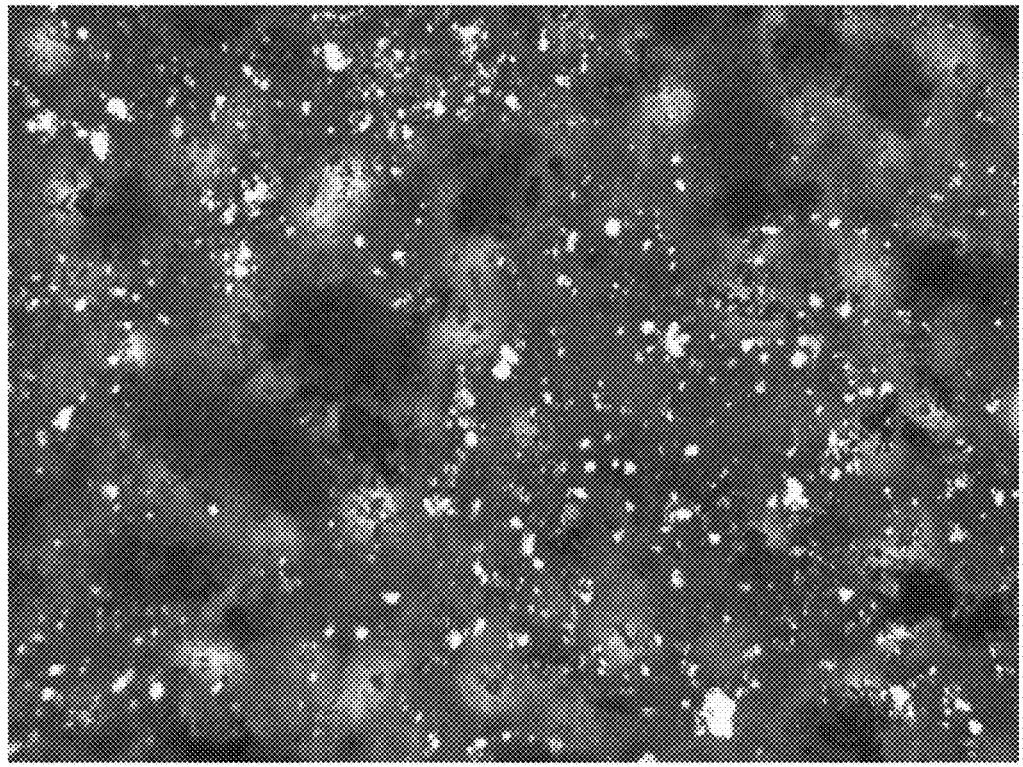
FIG. 13 shows the transition of dry GAL-101 Form II (intermediate stage 3).
Figure 14:
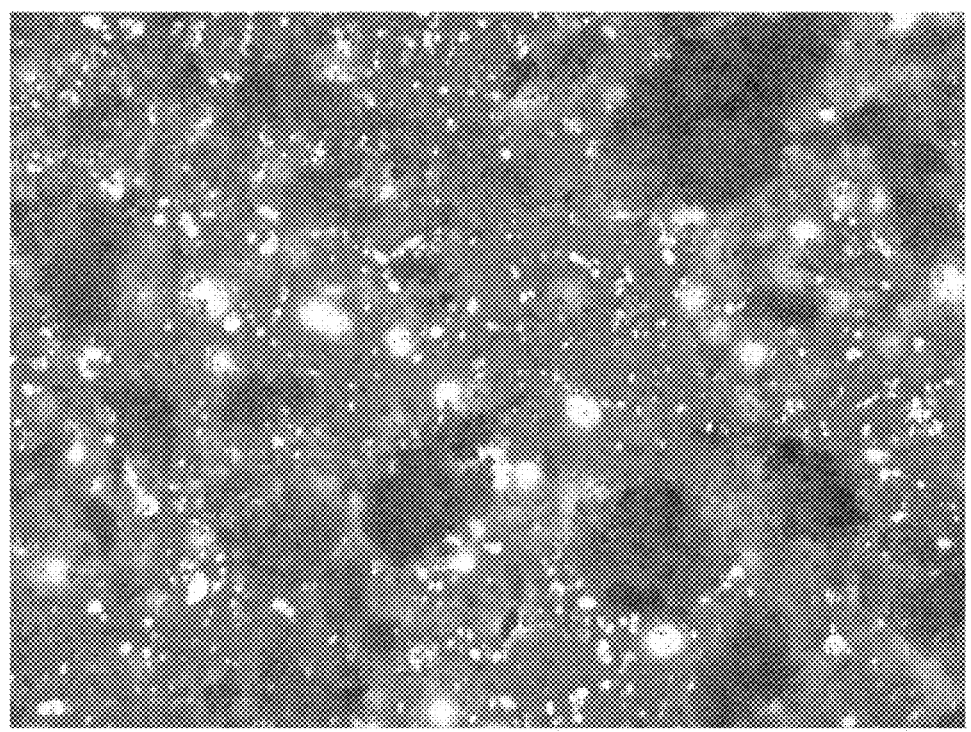
FIG. 14 shows the transition of dry GAL-101 Form II (finish).

The sample of Form II lost 7.94% of its weight in three consecutive steps. Some of the water (~3%) was absorbed on the surface of the crystals while the rest of the water (5%) was lost in two steps. The IR investigation of the product also supports the finding that Form II may be a hydrate. Due to the presence of the relatively large amount of water it was impossible to measure the heat effect of the phase transformation which was observed by XRPD around 60° C. These results are shown in FIG. 5.

Example 5

Microscopy Study of the Transition of Form II of (R)-2-[2-Amino-3-(indol-3-yl)propionylamino]-2-methylpropionic acid to Form I of (R)-2-[2-Amino-3-(indol-3-yl)propionylamino]-2-methylpropionic Acid Transition of wet Form II to Form I was observed through a MOTIC BA300 microscope (as shown in FIGS. 6-10) under polarized light. The transition of dry Form II to Form I was also studied (as shown in FIGS. 11-14). The transition from wet Form II to Form I proceeded rapidly. The large Form II crystals transformed to small crystals at 30-35° C. within 2 minutes. The crystals of Form II are large plates. The observed crystal form explains the observed thixotropic property of the suspension of Form II. Form I consists of uniform rounded crystals.

Example 6

Preparation of Form I of (R)-2-[2-Amino-3-(indol-3-yl)propionylamino]-2-methylpropionic Acid To a three necked 6 L flask equipped with overhead stirrer, thermometer, and pH meter, 1126.0 g (3.45 mol) of H-D-Trp-Aib-OH*HCl (purity by HPLC: 98.7 area %) was dissolved in 3378.5 mL of water (brown liquid was obtained). The reaction mixture was filtered through a glass filter to remove the mechanical contamination. The mixture was stirred at 20-25° C., and the pH of the solution was adjusted to 5.6 with 600.0 mL of a 20% NaOH solution maintaining the temperature at 20-25° C. The reaction mixture was warmed up to 30-35° C. for 3 hours. After 30 minutes stirring crystallization began and the resulting suspension was stirred at 20-25° C. overnight. The precipitate was collected by filtration. The cake was suspended in 1126.0 mL and 2252.0 mL of water and washed with 1126.0 mL of 2-propanol subsequently, then dried at 55-60° C. to constant weight.

Yield: 768.0 g (76.9%)

Purity: 98.7 area % by HPLC.

Appearance: off-white powder.

Example 7

Purification of (R)-2-[2-Amino-3-(indol-3-yl)propionylamino]-2-methylpropionic Acid Through the Isolation of Form H Step 1

To a three necked 6 L flask equipped with overhead stirrer, thermometer, and pH meter, 768.0 g (2.65 mol, 1.0 eq) of Form I (from Example 6 or Example 11, purity by IPC-HPLC: 98.7 area %) was dissolved in a mixture of 2140.0 mL of water and 268.0 mL of concentrated HCl (3.04 mol, 1.15 eq). The resulting brown solution was stirred at 5-10° C. and the pH was adjusted to 5.6 with 575.0 mL of a 20% NaOH solution maintaining the temperature at 5-10° C. After 30 minutes of stirring at 5-10° C., the crystallization began and the resulting suspension was stirred at 0-5° C. overnight. The precipitated Form II was collected by filtration and suspended in 2.0 L water then heated to 30-35° C. and stirred for 2 hours. The solid dissolved and precipitated again.

Monitoring: solubility test, the isolated precipitate was insoluble in water (the transformation of Form II to Form I was complete). The suspension was cooled to room temperature (20-25° C.), filtered and washed with 750 mL and 1500 mL water.

Yield (wet product): 1189.0 g. (IPC-HPLC: 99.59 area %)

Step 2

To a three necked 6 L flask equipped with overhead stirrer, thermometer, and pH meter, 1189.0 g of wet Form I from Step 1 was dissolved in a mixture of 1715.0 mL of water and 250.0 mL of concentrated HCl. The mixture was stirred at 5-10° C. and the pH of the solution was adjusted to 5.6 with 665.0 mL of a 20% NaOH solution maintaining the temperature at 5-10° C. After 30 minutes of stirring, the crystallization began. The resulting suspension was stirred at 0-5° C. overnight. The precipitate was collected by filtration. This collected Form II was suspended in 1.2 L of water and heated to 30-35° C. for two hours. At the beginning, the solid partly dissolved, then precipitated again. Solubility test (1.0 mL sample from the reaction mixture was diluted with 5.0 mL of deionized water, then vigorous stirring and the solubility was checked visually): the isolated precipitate was insoluble in water (The transformation of Form II to Form I was complete). The suspension was cooled to room temperature (20-25° C.), filtered and washed with 400 mL and 800 mL of water, subsequently then dried at 60-65° C. to constant weight.

Purity of the wet product by IPC-HPLC: 99.93 area %.
Yield: 34.1% (262.2 g)
Purity: 99.4 area % by HPLC.
Water content: 0.17%.
Appearance: white powder.

Example 8

Purification of (R)-2-[2-Amino-3-(indol-3-yl)propionylamino]-2-methylpropionic Acid Through the Isolation of Form H Step 1

To a three necked 6 L flask equipped with overhead stirrer, thermometer and pH meter 750.0 g (2.6 mol, 1 eq) of Form I (from Examples 6 and 11 with a purity by IPC-HPLC of about 98.5 area %) was dissolved in a mixture of 2085.0 mL of water and 262.5 mL of cc. HCl (2.99 mol, 1.15 eq).

The mixture (brown liquid) was stirred at 5-10° C. and the pH of the solution was adjusted to 5,6 with 535.0 mL of a 20% NaOH solution maintaining the temperature at 5-10° C. After 30 minutes stirring crystallization began and the resulting suspension was stirred at 0-5° C. for overnight. The precipitate (Form II) was collected by filtration. The collected Form II was suspended in 2.0 L of water and heated to 30-35° C. for two hours. At the beginning the solid partly dissolved, then precipitated again.

Solubility test: the isolated precipitate was insoluble in water (The transformation of Form II to Form I was complete). The suspension was cooled to room temperature (20-25° C.), filtered and washed with 500 mL and 1000 mL of water, subsequently.

The wet product was 1420.4 g. (IPC-HPLC:99.54 area %)

Step 2

To a three necked 6 L flask equipped with overhead stirrer, thermometer and pH meter 1420.4 g of wet product (Form I) from Step 1 was dissolved in a mixture of 1035.0 mL of water and 267.0 mL of concentrated HCl.

The mixture (brown liquid) was stirred at 5-10° C. and the pH of the solution was adjusted to 5.6 with 565.0 mL of a 20% NaOH solution at 5-10° C. After 30 minutes stirring crystallization began and the resulting suspension was stirred at 0-5° C. for overnight. The precipitate (Form II) was collected by filtration. The collected Form II was suspended in 1.4 L of water and heated to 30-35° C. for two hours. At the beginning the solid partly dissolved, then precipitated again.

Solubility test: the isolated precipitate was insoluble in water (The transformation of Form II to Form I was complete). The suspension was cooled to room temperature (20-25° C.), filtered and washed with 400 mL and 800 mL of water subsequently, then dried at 45-50° C. to constant weight by $P_2O_5$.

Purity of the wet product by IPC-HPLC: 99.85 area %.
Yield: 33.6% (252.3 g)
Purity:99.73 area % by HPLC.
Appearance: white powder.

Example 9

Purification of (R)-2-[2-Amino-3-(indol-3-yl)propionylamino]-2-methylpropionic Acid Through the Isolation of Form H To a three necked 4 L flask equipped with overhead stirrer, thermometer and pH meter 497.3 g (1.72 mol, 1 eq) of Form I (from Examples 6 and 11 with a purity by IPC-HPLC of about 98.5 area %) was dissolved in a mixture of 1380.0 mL of water and 173.5 mL of concentrated HCl (1.97 mol, 1.15 eq). The mixture was stirred at 5-10° C. and the pH of the solution was adjusted to 5.6 with 405.0 mL of a 20% NaOH solution maintaining at 5-10° C. After 30 minutes stirring crystallization began and the resulting suspension was stirred at 0-5° C. for overnight.

The precipitate (Form II) was collected by filtration. The collected Form II was suspended in 1.5 L of water and heated to 30-35° C. for two hours. At the beginning the solid partly dissolved, then precipitated again.

Solubility test: the isolated precipitate was insoluble in water (The transformation of Form II to Form I was complete).

The suspension was cooled to room temperature (20-25° C.), filtered and washed with 500 mL and 1000 mL of water subsequently then dried at 45-50° C. to constant weight.

Yield: 64.5% (321.0 g)

Purity: 99.81 area % by HPLC.

Appearance: white powder.

Example 10

Characterization of Form II of (R)-2-[2-Amino-3-(indol-3-yl)propionylamino]-2-methylpropionic Acid by Single Crystal X-Ray Diffraction The crystallization was done at Ubichem Research Ltd.

TABLE 5

| Crystallization Experiments by Evaporation | | | | |
|---|---|---|---|---|
| (R)-2-[2-Amino-3-(indol-3-yl)propionyl-amino]-2-methyl-propionic Acid (compound) | Solvent 1 | Solvent 2 | Solvent 3 | Observations |
| saturated in water ~0.4 mL | Methanol ~2 mL | Acetone ~2 mL | | The compound saturated in water. + methanol: no decrease in solubility + acetone: no supersaturation, no visible nucleation Slow evaporation from ampule, 1-2 crystals on the ampule wall |
| saturated in water + methanol ~0.5 mL | Methanol 4 mL | Acetone 1 mL | | Floating solid in the water-methanol mixture + Methanol dissolved the floating solid, acetone added Slowly evaporate from ampule, crystals grew on the wall of ampule, One crystal measured with X-ray diffr. |

TABLE 5-continued

Crystallization Experiments by Evaporation

| (R)-2-[2-Amino-3-(indol-3-yl)propionyl-amino]-2-methyl-propionic Acid (compound) | Solvent 1 | Solvent 2 | Solvent 3 | Observations |
|---|---|---|---|---|
| 25 mg/ more than solvable/ | Methanol 2 mL | Acetone 0.4 mL | Water 0.4 mL | Drawing the clear solution off; slowly evaporation of the solvent from ampule. 1-2 crystals grew here. The other part of the solution with floating compound is slowly evaporating from ampule (unclear solution). Crystals grew continuously of the solution liquid/air interface |

Summary of the Experiments

With water only: no crystals

With methanol only: 1-2 crystals, but too small for measurement

With methanol and water: no crystals

With methanol, water and other solvent: no single crystals

With methanol, water and acetone: Measurable single crystals, in the neck of the ampule Single Crystal X-Ray Diffraction Structure Elucidation The single crystal X-ray diffraction structure elucidation was performed by the Institute of Structural Chemistry, Chemical Research Center, Budapest.

Figure 15:
FIG. 15 shows a single crystal of GAL-101 Form II.

A crystal of Form II of compound (R)-2-[2-amino-3-(indol-3-yl)propionylamino]-2-methylpropionic acid (FIG. 15) was mounted on a loop. Cell parameters were determined by least-squares of the setting angles of 5232 (6.83°£q£47.20°) reflections. Intensity data were collected on an R-AXIS RAPID diffractometer (graphite monochromator; Cu-Ka radiation, l=1.54187 Å) at 293(2) K in the range 6.83°£q£47.20° using a scans.

A total of 7060 reflections were collected of which 1311 were unique [$R_{(int)}$=0.0323, R(sigma)=0.0411]; intensities of 1033 reflections were greater than 2s(I). Completeness to 2 q=0.996. An empirical absorption correction was applied to the data (the minimum and maximum transmission factors were 0.861 and 0.977). The structure was solved by direct methods.

Figure 16:
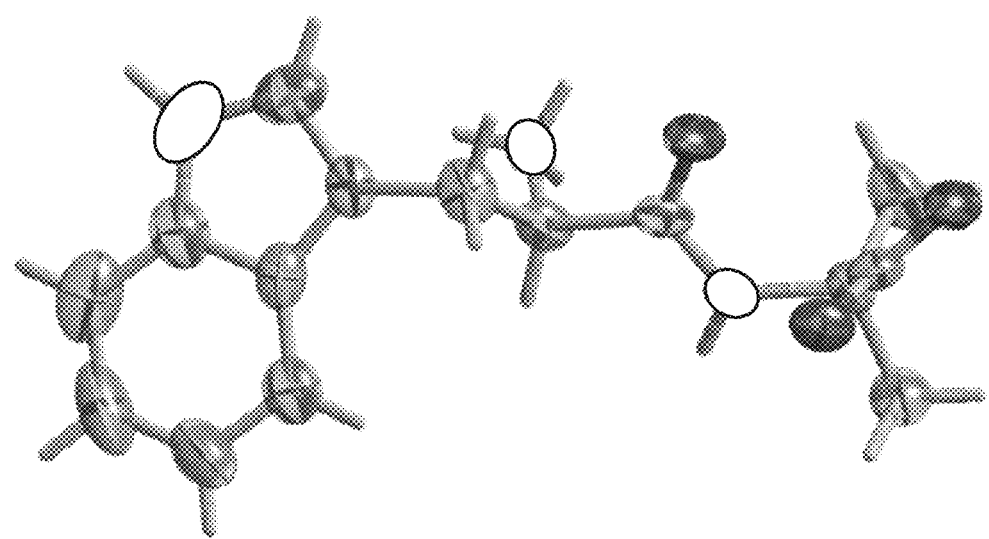
FIG. 16 shows the molecular structure in 50% probability displacement representation from the crystal of GAL-101 Form II. Configuration shown of the chiral center is (R).

Anisotropic full-matrix least-squares refinement on $F^2$ for all non-hydrogen atoms yielded $R_1$=0.0365 and $wR^2$=0.0687 for 1033 [I>2sigma(I)] and $R_1$=0.0564 and $wR^2$=0.0890 for all (1311) intensity data (goodness-of-fit=1.202; the maximum and mean shift/esd 0.000 and 0.000; extinction coefficient=0.0021(5)), number of parameters=194. The maximum and minimum residual electron density in the final difference map was 0.14 and −0.15e.Å3. Hydrogen atomic positions were calculated from assumed geometries except those on the cation that were located first in difference maps. Hydrogen atoms were included in structure factor calculations but they were not refined. The isotropic displacement parameters of the hydrogen atoms were approximated from the U(eq) value of the atom they were bonded. Final crystal structure model is shown in FIG. 16.

Results:

TABLE 6

Crystal Data

| | |
|---|---|
| Formula | $C_{15}H_{19}N_3O_3$ |
| Formula Weight | 289.33 |
| Crystal System | Orthorhombic |
| Space group | $P2_12_12_1$ (No. 19) |
| a, b, c [Angstrom] | 6.1316(2), 9.1342(2), 25.9213(7) |
| V [Ang**3] | 1451.78(7) |
| Z | 4 |
| D(calc) [g/cm**3] | 1.324 |
| Mu(CuKa) [ /mm ] | 0.769 |
| F(000) | 616 |
| Crystal Size [mm] | 0.03 × 0.08 × 0.20 |

Data Collection

| | |
|---|---|
| Temperature (K) | 294 |
| Radiation [Angstrom] | CuKa 1.54187 |
| Theta Min-Max [Deg] | 6.8, 47.2 |
| Dataset | −5: 5; −6: 8; −18: 24 |
| Tot., Uniq. Data, R(int) | 7060, 1311, 0.032 |
| Observed data [I > 2.0 sigma(I)] | 1033 |

Refinement

| | |
|---|---|
| Nref, Npar | 1311, 194 |
| R, wR2, S | 0.0365, 0.0890, 1.20 |
| | w = 1/[\s^2^(Fo^2^) + (0.0327P)^2^ + 0.3659P] where P = (Fo^2^+2Fc^2^)/3 |
| Max. and Av. Shift/Error | 0.00, 0.00 |
| Flack x | 0.2(5) |
| Hooft y | 0.3(2) |
| Min. and Max. Resd. Dens. [e/Ang^3] | −0.15, 0.14 |

Example 11

Preparation of Form I of (R)-2-[2-Amino-3-(indol-3-yl)propionylamino]-2-methylpropionic Acid The synthesis of GAL-101 Form I is performed via four chemical steps and a purification step as shown in Scheme 1.

Initially 2-aminoisobutyric acid tert-butyl ester (3) is liberated from its benzoate salt (1, Starting Material 1, Step 1) and then coupled with BOC-D-Tryptophan (2, Starting Material 2, Step 2). In Step 3 the totally protected API (4) is deprotected by means of hydrogen chloride and isolated as hydrochloride salt (5). In Step 4 the free form (GAL-101 Form I) is obtained in aqueous alkaline conditions. The crude API is purified by aqueous acidic dissolution, alkaline precipitation, isolation, and drying (synthesis procedure A8).

Step 1: Base Liberation tert-Butyl 2-aminoisobutyrate benzoate salt (1, analyzed against a predefined specification and released as Starting Material 1) is dissolved in aqueous sodium hydroxide—tert-butyl methyl ether (MTBE) system. The organic phase is separated and evaporated to dryness to give tert-butyl 2-aminoisobutyrate (3) as an oil.

Step 2: Coupling

BOC-D-Tryptophan (2, analysed against a predefined specification and released as Starting Material 2) and tert-butyl 2-aminoisobutyrate (3) are coupled by means of 4-(4,6-dimethoxy-1,3,5-triazin-2-yl)-4-methylmorpholine chloride (DMTMM) as coupling agent in ethyl acetate. Then the reaction mixture is washed with diluted aqueous solutions of citric acid, aqueous sodium carbonate solution and brine. The organic phase is concentrated to its one third volume and this solution of the protected API (4) is carried into the next step.

Step 3: Deprotection

Anhydrous deprotection is performed in ethyl acetate solution by means of hydrogen chloride gas. The precipitated hydrochloride salt (5) of the API is isolated by filtration.

Step 4: Liberation of GAL-101 Form I from its HCl Salt

The hydrochloride salt of GAL-101 Form I (5) is dissolved in deionised water and the pH of the solution is adjusted to 5.5-5.7 by 10% aqueous sodium hydroxide solution. The crude API is precipitated at 30-35° C. to obtain a stable crystal form and filtered off.

Scheme 1: Synthesis of GAL-101 Form I

Starting Material 1

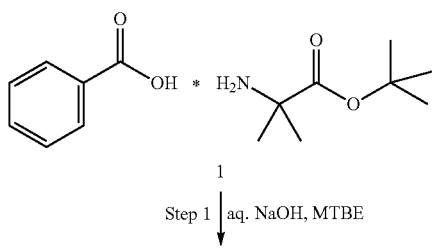

1

Step 1 | aq. NaOH, MTBE

Starting Material 2

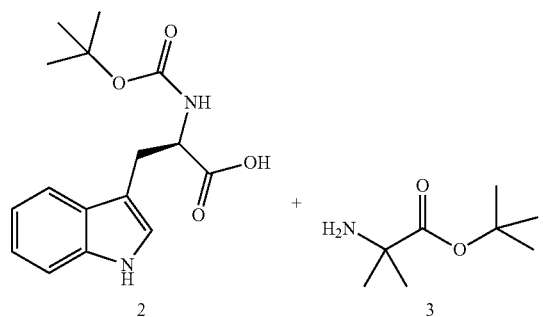

2 + 3

Step 2 | 1. DMTMM, EtOAc
2. aq. citric acid, aq. Na$_2$CO$_3$, brine
3. evaporation

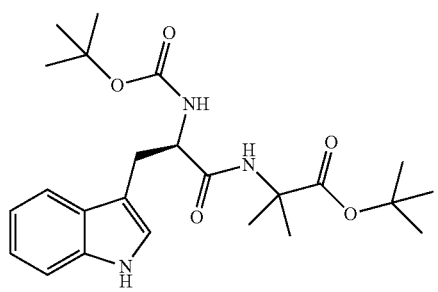

4

Step 3 | HCl gas, EtOAc

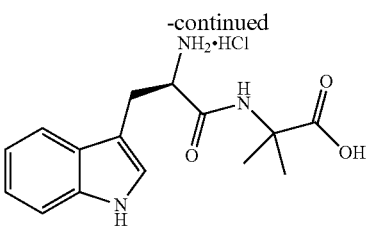

5

Step 4 Purification | 1. aq. NaOH
2. aq. HCl, NaOH, DI water, EtOH

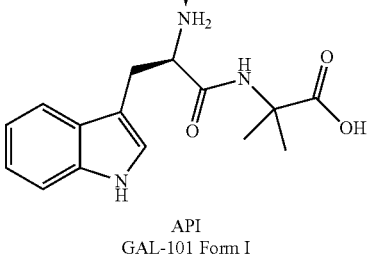

API
GAL-101 Form I

Purification

The crude drug substance GAL-lot Form I is dissolved in diluted hydrochloric acid, filtered through a 0.5µ filter, then precipitated by addition of 10% aqueous sodium hydroxide solution adjusting the pH 5.5 to 5.7. The precipitate is suspended in deionised water, then ethanol and subsequently dried in vacuo at elevated temperature (max. 40° C.).

TABLE 7

Changes in processes for synthesizing GAL-101 Form I

| Batch (Salt) | Batch number | Procedure | Quantity | Purity/ optical purity* |
|---|---|---|---|---|
| 8 (free form) | CT-1105.07 | A0 | 54 g | 98.2% 99.9% |
| 10 (HCl) | AK-10235.07 | A1 | 159 g | 98.7% 100% |
| 21 (HCl) | 2/1308/02/00858 | A3 | 1.26 kg | 96.6% 99.9% |
| 30 (HCl) | 2/1308/03/00940 | A3 | 8.72 kg | 98.7% 99.9% |
| 31/32 (HCl) | 2/1308/03/00905 | A4 | 1.38 kg | 97.4% 99.9% |
| 35 (free form) | 2/1308/04/00965 | A5 | 5.33 kg | 98.5% 99.9% |
| 36 (free form) | 2/1308/04/00971 | A6 | 24.0 kg | 98.6% 99.2% |
| 37 (free form) | 2/1308/04/00985 | A7 | 19.30 kg | 98.8% 99.7% |
| 40 (free form) pilot batch | 2015/1308/01139 | A8 | 2.52 kg | 99.7% 99.8% |
| 44 (free form) GMP | 2290/1308/01604 | A8 | 2.88 kg | 99.5% 99.8% |
| 45 (free form) GMP | 2290/1308/01605 | A8 | 2.65 kg | 99.5% 99.8% |

*determined by HPLC (area %)

In Step 3, the precipitation of the hydrochloride salt was facilitated with the addition of n-heptane. In Step 4, the free form was liberated by means of propylene oxide in tetrahydrofuran. Then the precipitated base was treated with acetonitrile, filtered off and recrystallized from 2-propanol.

A1: Modifications of the Synthesis Procedure A0
  a) The hydrochloride salt was prepared. The liberation of the free form (Step 4) was not carried out.
A2: Modifications of the Synthesis Procedure A1
  b) Hexane was used instead of heptane in Step 3. No significant effect on yield and quality was observed.
A3: Modifications of the Synthesis Procedure A2
  c) Hexane was not used in Step 3 to facilitate the precipitation of the hydrochloride salt, only for washing the wet product. No significant effect on yield and quality was observed.
A4: Modifications of the Synthesis Procedure A3
  d) Purification procedure for Intermediate 4 was introduced in the process. Intermediate 4 was dissolved in dichloromethane and washed with aqueous sodium carbonate solution. Then dichloromethane was exchanged to ethyl acetate. The chiral purity of starting material 2 was low (96.1%), with this modification the chiral purity of intermediate 4 was increased.
A5: Modifications of the Synthesis Procedure A4
  e) In Step 4 the free form was obtained from alkaline aqueous sodium hydroxide solution at pH 5.6. The base was filtered off and washed with water and 2-propanol. The free base showed similar quality as the HCl salt and the yield of liberation was 68%.
A6: Modifications of the Synthesis Procedure A5
  f) In Step 3 the wet hydrochloride salt was washed with toluene. This procedure was not implemented into the next campaigns.
  g) In Step 4 the free form was further purified, dissolved in diluted hydrochloric acid and precipitated by addition of 20% aqueous sodium hydroxide solution at pH 5.6. The yield of purification was increased to 78%.
  h) The wet base was washed with water only.
A7: Modifications of the Synthesis Procedure A6
  i) In Step 3 the wet hydrochloride salt was not washed with toluene.
A8: Modifications of the Synthesis Procedure A7
  j) In Step 3 the cleavage was performed in diluted conditions (8×EtOAc instead of 3×). The purity of the API was improved, and the procedure was implemented into the next campaigns.
  k) In Step 4 the wet product was also washed with ethanol (after water washing) after the purification of the API to remove most of water and facilitate drying.

Example 12 (Based on Example 9)

Preparation of GAL-101 Form I

To a three necked 4 L flask equipped with overhead stirrer, thermometer and pH meter 497.3 g (1.72 mol, 1 eq) of GAL-101 (e.g., from Examples 6 and 11 with a purity by IPC-HPLC of about 98.5 area %) was dissolved in a mixture of 1380.0 mL of water and 173.5 mL of concentrated HCl (1.97 mol, 1.15 eq). The mixture was stirred at 5-10° C. and the pH of the solution was adjusted to 5.6 with 405.0 mL of a 20% NaOH solution maintaining at 5-10° C. After 30 minutes stirring crystallization began and the resulting suspension was stirred at 0-5° C. for overnight.

The precipitate (GAL-101 Form II) was collected by filtration. The collected GAL-101 Form II was suspended in 1.5 L of water and heated to 30-35° C. for two hours. At the beginning the solid partly dissolved, then precipitated again.

Solubility test: the isolated precipitate was insoluble in water (The transformation of GAL-101 Form II to GAL-101 Form I was complete).

The suspension was cooled to room temperature (20-25° C.), filtered and washed with 500 mL and 1000 mL of water subsequently then dried at 45-50° C. to constant weight.
  Yield: 64.5% (321.0 g)
  Purity: 99.81 area % by HPLC.
  Appearance: white powder.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. Form II of (R)-2-[2-amino-3-(indol-3-yl)propionylamino]-2-methylpropionic acid, characterized by an X-ray powder diffraction pattern displaying peaks at °2θ (d value Å) angles of 5.87 (15.067), 11.91(7.432), 17.99 (4.931), 30.35 (2.945).

2. The Form II of claim 1, which exhibits the FT-IR spectrum as shown in FIG. 1, and/or the X-ray powder diffraction pattern as shown in FIG. 2.

3. Form II of (R)-2-[2-amino-3-(indol-3-yl)propionylamino]-2-methylpropionic acid, characterized by a single crystal X-ray diffraction pattern having an orthorhombic crystal system and a space group of P $2_12_12_1$.

4. The Form II of claim 3, wherein the orthorhombic crystal system has a dimension of a=6.1316(2)Å; b=9.1342 (2)Å; and c=25.9213(7)Å.

5. A process for preparing Form II of (R)-2-[2-amino-3-(indol-3-yl)propionylamino]-2-methylpropionic acid of claim 1, comprising
  (a) mixing Form I of (R)-2-[2-amino-3-(indol-3-yl)propionylamino]-2-methylpropionic acid with an aqueous HCl to provide a solution of the compound;
  (b) cooling the solution to about 0-5° C., followed by adjusting the pH of the solution to about 5.6 with a base;
  (c) stirring the solution at about 0-5° C. until precipitation is complete; and
  (d) isolating the resulting precipitate to give the Form II of compound (R)-2-[2-amino-3-(indol-3-yl)propionylamino]-2-methylpropionic acid;
  (e) optionally drying the isolated precipitate at 0-5° C. by a drying agent.

6. The process of claim 5, wherein said Form I of the compound is characterized by an X-ray powder diffraction pattern displaying peaks at °2θ (d value Å) angles 6.75 (13.095), 10.19 (8.678), 11.76 (7.524), 13.56 (6.531), 17.68 (5.017), 18.63 (4.764), 20.15 (4.407), 22.08 (4.026).

7. Form II of (R)-2-[2-amino-3-(indol-3-yl)propionylamino]-2-methylpropionic acid prepared by the process of claim 5.

8. A method of preparing ultrapure Form I of compound (R)-2-[2-amino-3-(indol-3-yl)propionylamino]-2-methylpropionic acid, characterized by an X-ray powder diffraction pattern displaying peaks at °2θ (d value Å) angles 6.75 (13.095), 10.19 (8.678), 11.76 (7.524), 13.56 (6.531), 17.68 (5.017), 18.63 (4.764), 20.15 (4.407), 22.08 (4.026), wherein the purity of the ultrapure Form I of the compound is from about 99.70 area % to about 99.999 area % by IPC-HPLC, the method comprising
  (a) mixing Form II of the compound with water to prepare a solution of Form II of the compound;
  (b) heating the solution of Form II to about 30-35° C. and cooling to room temperature to produce a precipitate; and (c) isolating and washing the precipitate to give ultrapure Form I of compound (R)-2-[2-amino-3-(indol-3-yl)propionylamino]-2-methylpropionic acid;

(d) optionally drying the precipitate at about 45-50° C.

wherein the purity of the ultrapure Form I of the compound is from about 99.70 area % to about 99.999 area % by IPC-HPLC.

9. A method for preparing ultrapure Form I of (R)-2-[2-amino-3-(indol-3-yl)propionylamino]-2-methylpropionic acid, characterized by an X-ray powder diffraction pattern displaying peaks at °2θ (d value Å) angles 6.75 (13.095), 10.19 (8.678), 11.76 (7.524), 13.56 (6.531), 17.68 (5.017), 18.63 (4.764), 20.15 (4.407), 22.08 (4.026), wherein said ultrapure Form I of the compound has a purity of from about 99.70 area % to about 99.999 area % by IPC-HPLC, the method comprising (a) mixing compound (R)-2-[2-amino-3-(indol-3-yl)propionylamino]-2-methylpropionic acid with an aqueous HCl to provide a solution of the compound;

(b) cooling the solution to about 5-10° C., followed by adjusting the pH of the solution to about 5.6 with a base;

(c) stirring the solution at about 0-5° C. until precipitation is complete;

(d) isolating the resulting precipitate to obtain Form II of the compound;

(e) mixing the Form II of the compound of step (d) with water to prepare a solution of Form II of the compound;

(f) heating the solution of Form II of step (e) to about 30-35° C. and cooling to room temperature to produce a precipitate; and (g) isolating and washing the precipitate to give an ultrapure Form I of the compound;

wherein the washing step is optionally repeated for two or three times;

(h) optionally drying at about 45-50° C.; and (i) optionally repeating steps (a) to (h).

10. The method of claim 9, wherein said compound (R)-2-[2-amino-3-(indol-3-yl)propionylamino]-2-methylpropionic acid of step (a) is prepared by the steps comprising (a) reacting compound (2)

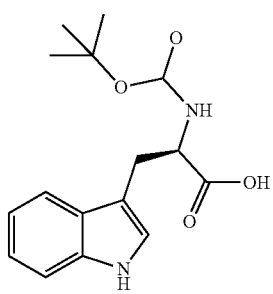

with tert-butyl2-aminoisobutyrate (3) in the presence of 4-(4,6-dimethoxy-1,3,5-triazin-2-yl)-4-methylmorpholine chloride (DMTMM) to give compound (4)

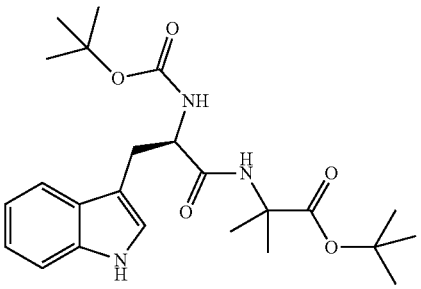

(b) removing the Boc group from compound 4 with hydrogen chloride gas to give compound (5); and

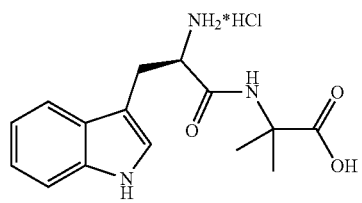

(c) providing a solution of compound (5) in water and adjusting the pH of the solution to about 5.5-5.7 to give compound (R)-2-[2-amino-3-(indol-3-yl)propionylamino]-2-methylpropionic acid.

11. The method of claim 10, optionally further comprising a step of purifying the compound (R)-2-[2-amino-3-(indol-3-yl)propionylamino]-2-methylpropionic acid from step (c) by (a) dissolving compound (R)-2-[2-amino-3-(indol-3-yl)propionylamino]-2-methylpropionic acid in 5M HCl to provide a HCl solution of the compound and filtering;

(b) adjusting the pH of the filtered solution to about 5.5-5.7 by 10% aqueous NaOH to give a precipitate; and (c) washing the precipitate with water and ethanol and dried.

12. A composition comprising Form II of claim 1 and a pharmaceutically acceptable carrier or excipient.

13. A process for preparing Form II of (R)-2-[2-amino-3-(indol-3-yl)propionylamino]-2-methylpropionic acid of claim 1, comprising (a) reacting compound (2)

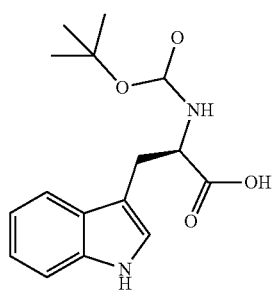

with tert-butyl-2-aminoisobutyrate (3) in the presence of 4-(4,6-dimethoxy-1,3,5-triazin-2-yl)-4-methylmorpholine chloride (DMTMM) to give compound (4)

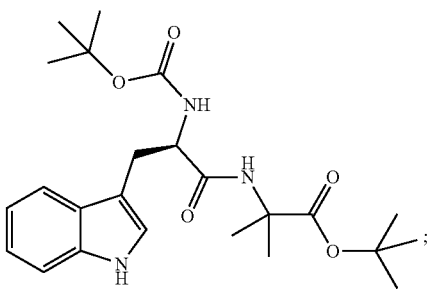 [SMILES: CC(C)(C)OC(=O)N[C@H](Cc1c[nH]c2ccccc12)C(=O)NC(C)(C)C(=O)OC(C)(C)C]

(b) removing the Boc group from compound (4) with hydrogen chloride gas to give compound (5);

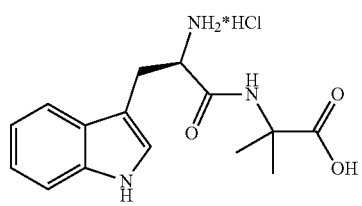

(c) providing a solution of compound (5) in water and adjusting the pH of the solution to about 5.5-5.7 to give a precipitate;

(d) mixing the precipitate from step (c) with an aqueous HCl to provide a solution;

(e) cooling the solution of step (d) to about 0-5° C., followed by adjusting the pH of the solution to about 5.6 with a 20% NaOH aqueous solution (f) stirring the solution at about 0-5° C. until precipitation is complete; and (g) isolating the resulting precipitate to give Form II of compound (R)-2-[2-amino-3-(indol-3-yl)propionylamino]-2-methylpropionic acid.

(h) optionally drying the isolated precipitate at 0-5° C. by a drying agent.

14. A composition comprising Form II of claim 7 and a pharmaceutically acceptable carrier or excipient.

* * * * *